(12) United States Patent
Srivastava et al.

(10) Patent No.: US 10,501,801 B2
(45) Date of Patent: Dec. 10, 2019

(54) IDENTIFICATION OF TUMOR-PROTECTIVE EPITOPES FOR THE TREATMENT OF CANCERS

(71) Applicant: THE UNIVERSITY OF CONNECTICUT, Farmington, CT (US)

(72) Inventors: Pramod K. Srivastava, Avon, CT (US); Ion Mandoiu, Storrs, CT (US); Fei Duan, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 389 days.

(21) Appl. No.: 14/431,093

(22) PCT Filed: Sep. 27, 2013

(86) PCT No.: PCT/US2013/062100
§ 371 (c)(1),
(2) Date: Mar. 25, 2015

(87) PCT Pub. No.: WO2014/052707
PCT Pub. Date: Apr. 3, 2014

(65) Prior Publication Data
US 2015/0252427 A1  Sep. 10, 2015

Related U.S. Application Data

(60) Provisional application No. 61/707,295, filed on Sep. 28, 2012.

(51) Int. Cl.
G06F 19/18 (2011.01)
C12Q 1/6886 (2018.01)
(Continued)

(52) U.S. Cl.
CPC ........ *C12Q 1/6886* (2013.01); *A61K 39/0011* (2013.01); *G16H 50/20* (2018.01);
(Continued)

(58) Field of Classification Search
None
See application file for complete search history.

(56) References Cited

U.S. PATENT DOCUMENTS

| 8,140,270 B2 | 3/2012 | Kingsmore et al. |
| 2009/0098533 A1 | 4/2009 | Munnes et al. |

(Continued)

FOREIGN PATENT DOCUMENTS

| WO | 2011143656 A2 | 11/2011 |
| WO | 2014052707 A2 | 4/2014 |
| WO | 2012159754 A2 | 11/2016 |

OTHER PUBLICATIONS

Stephens et al. The landscape of cancer genes and mutational processin breast cancer. Nature, 2012, vol. 486, p. 400-404.*

(Continued)

*Primary Examiner* — Olivia M. Wise
(74) *Attorney, Agent, or Firm* — Cantor Colburn LLP

(57) ABSTRACT

Described herein are methods of identifying tumor-specific epitopes from the cancer tissue DNA of cancer patients using both DNA sequencing and bioinformatics techniques. The identification of tumor-specific epitopes provides pharmaceutical compositions with a limited number of tumor-specific peptides suitable for personalized genomics-driven immunotherapy of human cancer. Specifically disclosed herein is a novel index called the Differential Agretopic Index (DAI) for the epitope which allows prediction of whether immunization with a particular epitope will be (Continued)

protective against the tumor. Pharmaceutical compositions and methods of administration are also included.

17 Claims, 10 Drawing Sheets

Specification includes a Sequence Listing.

(51) Int. Cl.
  *A61K 39/00*   (2006.01)
  *G16H 50/20*   (2018.01)
(52) U.S. Cl.
  CPC .............. *A61K 2039/55561* (2013.01); *C12Q 2600/106* (2013.01); *C12Q 2600/112* (2013.01); *C12Q 2600/158* (2013.01)

(56) References Cited

U.S. PATENT DOCUMENTS

2011/0257890 A1  10/2011  Weinschenk et al.
2011/0293637 A1  12/2011  Hacohen et al.

OTHER PUBLICATIONS

Kreiter et al. Targeting the tumor mutanome for personalized vaccination therapy. OncoImmunology, 2012, vol. 1, Issue 5, p. 768-769.*
Castle et al. Exploiting the Mutanome for Tumor Vaccination. Microenvironment and Immunology, 2012, vol. 72, p. 1081-1091.*
Assarsson et al.; "A Quantitative Analysis of the Variables Affecting the Repertoire of T Cell Specificities Recognized after Vaccinia Virus Infection"; J Immunol/ 178; pp. 7890-7901; (2007).
Castle et al.; "Exploiting the Mutanome for Tumor Vaccination"; Cancer Res. 72; ppp 1081-1091; (2012).
Duan et al.; "Genomic and Bioinformatic Profiling of Mutational Neoepitopes Reveals New Rules to Predict Anticancer Immunogenicity"; J. Exp Med; 211; pp. 2231-2248; (2014).
Segal et al.; "Epitope Landscape in Breast and Colorectal Cancer"; Cancer Res; 68(3); pp. 889-892; (2008).
Srivastava et al.; "Modeling the Repertoire of True Tumor-Specific MHC 1 Epitopes in a Human Tumor"; PLoS One; 4; e6094; pp. 1-7 (2009).
13840946.1 Extended Search Report dated Sep. 2, 2016; 11 pages.
Fortier et al.; "The MHC Class I Peptide Repertoire is Molded by the Transcriptome"; The Journal of Experimental Medicine; 205(3); pp. 595-610; (2008).
International Search Report and Written Opinion; International Application No. PCT/US13/62100; International Filing Date Sep. 27, 2013; dated Jan. 8, 2014; 18 pages.
International Preliminary Report on Patentability; International Application No. PCT/US2013/062100; International Filing Date Sep. 27, 2013; dated May 7, 2015; 9 pages.
Fritsch et al; "HLA-Binding Properties of Tumor Neoepitopes in Humans"; Cancer Immunology Res.; 2(6); pp. 522-529; (2014).
Jorgensen et al.; "NetMHCstab [ Predicting Stability of Peptide-MHC-1 Complexes; Impacts for Cytotoxic T Lymphocyte Epitope Discovery"; Immunology; 141; pp. 18-26 (2013).
Rech et al.; "Tumor Immunity and Survival as a Function of Alternative Neopeptides in Human Cancer"; Cancer Immunology Research, 6(3) 1-12, Mar. 2018; Published OnlineFirst Jan. 16, 2018.
Massive Parallel Sequencing from Wikipedia; available under the Creative Commons Attribution_ShareAlike License; 7 pages; https://en.wikipedia.org/w/index.php?title=Massive_parallel_sequencing &oldid=853277093; printed Sep. 2018.
Third Party Obseration for Application No. EP20130840946, 15 pages; submitted on Sep. 18, 2018.
Ghorani et al.; "Differential Binding Affinity of Mutated Peptides for MHC Class I is a Predictor of Survival in Advanced Lung Cancer and Melanoma"; Annals of Oncology, 29; pp. 271-279; (2018).
Borbulevych, Oleg Y., et al., "Structures of MART-1 26/27~35 Peptide/HLA-A2 Complexes Reveal a Remarkable Disconnect between Antigen Structural Homology and T Cell Recognition", J. Mol. Biol., 2007, vol. 372, No. 5, pp. 1123-1136.
Fritsch, Edward F., "HLA-Binding Properties of Tumor Neoepitopes in Humans", Cancer Immunol. Res., Mar. 2014, vol. 2, No. 6, pp. 522-529.
Jorgensen, Kasper W. et al., "NetMHCSTAB—predicting stability of peptide-MHC-I complexes; impacts for cytoxic T lymphocyte epitope discovery", Immunology, 2013, vol. 141, pp. 18-26.
Knapp, Bernhard, "3-Layer-based analysis of peptide-MHC interaction: In silico prediction, peptide binding affinity and T cell activation in a relevant allergen-specific model", Molecular Immunology, 2009, vol. 46, pp. 1839-1844.
Priyadarshini, Vani et al., "Genome-based approaches to develop epitope-driven subunit vaccines against pathogens of infective endocarditis", Journal of BiomolecularStructure and Dynamics, Apr. 2014, vol. 32, No. 6, pp. 876-889.

* cited by examiner

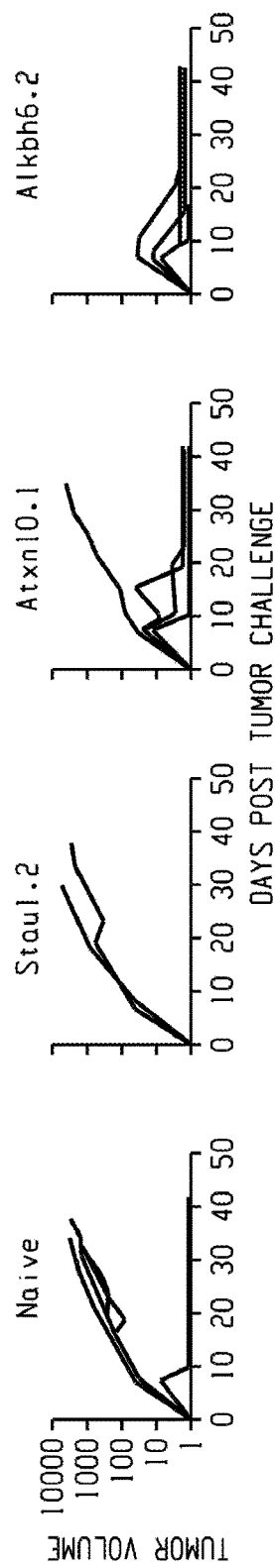
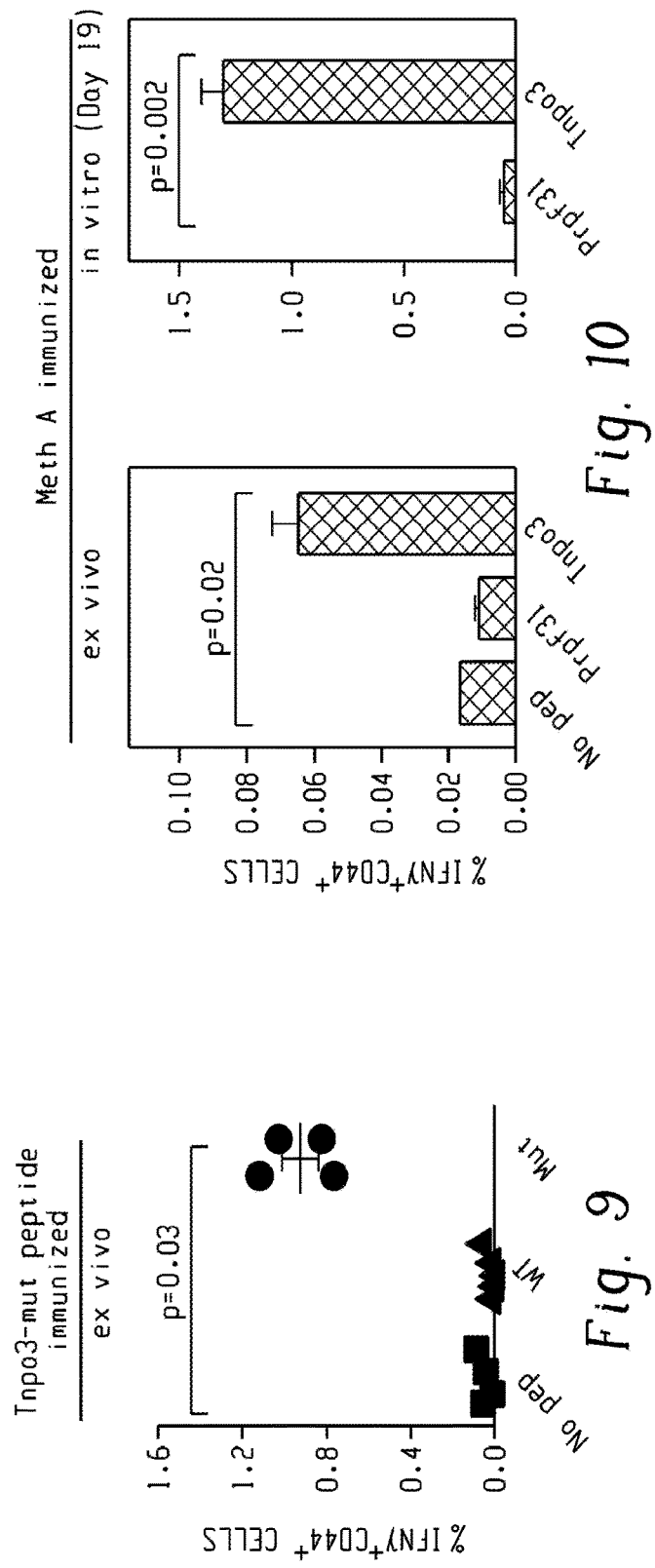
Fig. 8
Fig. 9
Fig. 10

SEQUENCE LISTING

<160> NUMBER OF SEQ ID NOS: 129

<210> SEQ ID NO 1
<211> LENGTH: 9
<212> TYPE: PRT
<213> ORGANISM: Mus musculus

<400> SEQUENCE: 1

Lys Phe Asn Pro Met Phe Thr Tyr Ile
1               5

<210> SEQ ID NO 2
<211> LENGTH: 9
<212> TYPE: PRT
<213> ORGANISM: Mus musculus

<400> SEQUENCE: 2

Cys Tyr Ala Lys Val Lys Glu Gln Leu
1               5

<210> SEQ ID NO 3
<211> LENGTH: 9
<212> TYPE: PRT
<213> ORGANISM: Mus musculus

<400> SEQUENCE: 3

Cys Tyr Ala Lys Leu Lys Glu Gln Leu
1               5

<210> SEQ ID NO 4
<211> LENGTH: 9
<212> TYPE: PRT
<213> ORGANISM: Mus musculus

<400> SEQUENCE: 4

Lys Tyr Ile His Ser Ala Asn Val Leu
1               5

<210> SEQ ID NO 5
<211> LENGTH: 9
<212> TYPE: PRT
<213> ORGANISM: Mus musculus

<400> SEQUENCE: 5

Lys Tyr Ile His Ser Ala Asn Val Leu
1               5

<210> SEQ ID NO 6
<211> LENGTH: 11
<212> TYPE: PRT
<213> ORGANISM: Mus musculus

<400> SEQUENCE: 6

His Tyr Val His Ile Ile Glu Ser Lys Pro Leu
1               5                   10

<210> SEQ ID NO 7
<211> LENGTH: 11
<212> TYPE: PRT
<213> ORGANISM: Mus musculus

<400> SEQUENCE: 7

His Tyr Val His Ile Ile Glu Ser Lys Pro Leu
1               5                   10

<210> SEQ ID NO 8
<211> LENGTH: 10
<212> TYPE: PRT
<213> ORGANISM: Mus musculus

<400> SEQUENCE: 8

His Tyr Leu Gln Tyr Lys Gln Glu Asp Leu
1               5                   10

<210> SEQ ID NO 9
<211> LENGTH: 10
<212> TYPE: PRT
<213> ORGANISM: Mus musculus

<400> SEQUENCE: 9

Gln Tyr Leu Gln Tyr Lys Gln Glu Asp Leu
1               5                   10

<210> SEQ ID NO 10
<211> LENGTH: 8
<212> TYPE: PRT
<213> ORGANISM: Mus musculus

<400> SEQUENCE: 10

Gln Tyr Ile His Ser Ala Asn Val
1               5

<210> SEQ ID NO 11
<211> LENGTH: 8
<212> TYPE: PRT
<213> ORGANISM: Mus musculus

<400> SEQUENCE: 11

Lys Tyr Ile His Ser Ala Asn Val
1               5

<210> SEQ ID NO 12
<211> LENGTH: 11
<212> TYPE: PRT
<213> ORGANISM: Mus musculus

<400> SEQUENCE: 12

Leu Tyr Gln Ile Leu Arg Gly Leu Gln Tyr Ile
1               5                   10

<210> SEQ ID NO 13
<211> LENGTH: 11
<212> TYPE: PRT
<213> ORGANISM: Mus musculus

<400> SEQUENCE: 13

Leu Tyr Gln Ile Leu Arg Gly Leu Lys Tyr Ile
1               5                   10

<210> SEQ ID NO 14
<211> LENGTH: 11
<212> TYPE: PRT
<213> ORGANISM: Mus musculus

<400> SEQUENCE: 14

Asn Tyr Leu Leu Ser Leu Val Ala Val Met Leu
1               5                   10

<210> SEQ ID NO 15

```
<211> LENGTH: 11
<212> TYPE: PRT
<213> ORGANISM: Mus musculus

<400> SEQUENCE: 15

Asn Tyr Leu Leu Ser Leu Val Ala Val Val Leu
1               5                   10

<210> SEQ ID NO 16
<211> LENGTH: 8
<212> TYPE: PRT
<213> ORGANISM: Mus musculus

<400> SEQUENCE: 16

Ser Tyr Leu Val Val Phe Pro Leu
1               5

<210> SEQ ID NO 17
<211> LENGTH: 8
<212> TYPE: PRT
<213> ORGANISM: Mus musculus

<400> SEQUENCE: 17

Ser Tyr Arg Val Val Phe Pro Leu
1               5

<210> SEQ ID NO 18
<211> LENGTH: 11
<212> TYPE: PRT
<213> ORGANISM: Mus musculus

<400> SEQUENCE: 18

Gln Tyr Ser Gly Ser Trp Val Glu Thr Pro Val
1               5                   10

<210> SEQ ID NO 19
<211> LENGTH: 11
<212> TYPE: PRT
<213> ORGANISM: Mus musculus

<400> SEQUENCE: 19

Gln Tyr Ser Gly Ser Arg Val Glu Thr Pro Val
1               5                   10

<210> SEQ ID NO 20
<211> LENGTH: 9
<212> TYPE: PRT
<213> ORGANISM: Mus musculus

<400> SEQUENCE: 20

His Tyr Ile Asn Met Ile Leu Pro Ile
1               5

<210> SEQ ID NO 21
<211> LENGTH: 9
<212> TYPE: PRT
<213> ORGANISM: Mus musculus

<400> SEQUENCE: 21

His Tyr Ile Asn Met Ser Leu Pro Ile
1               5

<210> SEQ ID NO 22
<211> LENGTH: 9
<212> TYPE: PRT
```

-continued

```
<213> ORGANISM: Mus musculus

<400> SEQUENCE: 22

Ala Tyr Cys Glu Thr Cys Trp Glu Leu
1               5

<210> SEQ ID NO 23
<211> LENGTH: 9
<212> TYPE: PRT
<213> ORGANISM: Mus musculus

<400> SEQUENCE: 23

Ala Tyr Cys Glu Thr Cys Trp Glu Trp
1               5

<210> SEQ ID NO 24
<211> LENGTH: 11
<212> TYPE: PRT
<213> ORGANISM: Mus musculus

<400> SEQUENCE: 24

Ser Tyr Leu Leu Gly Ser Gly Glu Ala Arg Leu
1               5                   10

<210> SEQ ID NO 25
<211> LENGTH: 11
<212> TYPE: PRT
<213> ORGANISM: Mus musculus

<400> SEQUENCE: 25

Ser Tyr Gln Leu Gly Ser Gly Glu Ala Arg Leu
1               5                   10

<210> SEQ ID NO 26
<211> LENGTH: 10
<212> TYPE: PRT
<213> ORGANISM: Mus musculus

<400> SEQUENCE: 26

Thr Tyr Ile Arg Pro Phe Glu Thr Lys Val
1               5                   10

<210> SEQ ID NO 27
<211> LENGTH: 10
<212> TYPE: PRT
<213> ORGANISM: Mus musculus

<400> SEQUENCE: 27

Thr Tyr Ile Arg Pro Leu Glu Thr Lys Val
1               5                   10

<210> SEQ ID NO 28
<211> LENGTH: 9
<212> TYPE: PRT
<213> ORGANISM: Mus musculus

<400> SEQUENCE: 28

His Tyr Leu Ser Ser Ile Leu Arg Leu
1               5

<210> SEQ ID NO 29
<211> LENGTH: 9
<212> TYPE: PRT
<213> ORGANISM: Mus musculus
```

<400> SEQUENCE: 29

His Tyr Leu Ser Ala Ile Leu Arg Leu
1               5

<210> SEQ ID NO 30
<211> LENGTH: 11
<212> TYPE: PRT
<213> ORGANISM: Mus musculus

<400> SEQUENCE: 30

Leu Tyr Leu Asp Ser Lys Ser Asp Thr Thr Val
1               5                   10

<210> SEQ ID NO 31
<211> LENGTH: 11
<212> TYPE: PRT
<213> ORGANISM: Mus musculus

<400> SEQUENCE: 31

Ser Tyr Leu Asp Ser Lys Ser Asp Thr Thr Val
1               5                   10

<210> SEQ ID NO 32
<211> LENGTH: 11
<212> TYPE: PRT
<213> ORGANISM: Mus musculus

<400> SEQUENCE: 32

Tyr Tyr Val Pro Leu Leu Lys Arg Val Pro Leu
1               5                   10

<210> SEQ ID NO 33
<211> LENGTH: 11
<212> TYPE: PRT
<213> ORGANISM: Mus musculus

<400> SEQUENCE: 33

Tyr Tyr Val Pro Leu Leu Lys Arg Val Pro Ser
1               5                   10

<210> SEQ ID NO 34
<211> LENGTH: 10
<212> TYPE: PRT
<213> ORGANISM: Mus musculus

<400> SEQUENCE: 34

Lys Tyr Met Ser Met Leu Glu Glu Arg Ile
1               5                   10

<210> SEQ ID NO 35
<211> LENGTH: 10
<212> TYPE: PRT
<213> ORGANISM: Mus musculus

<400> SEQUENCE: 35

Lys Asp Met Ser Met Leu Glu Glu Arg Ile
1               5                   10

<210> SEQ ID NO 36
<211> LENGTH: 11
<212> TYPE: PRT
<213> ORGANISM: Mus musculus

<400> SEQUENCE: 36

Gly Tyr Phe Val Ser Lys Ala Lys Thr Ser Val
1               5                   10

<210> SEQ ID NO 37
<211> LENGTH: 11
<212> TYPE: PRT
<213> ORGANISM: Mus musculus

<400> SEQUENCE: 37

Gly Tyr Phe Val Ser Lys Ala Lys Thr Arg Val
1               5                   10

<210> SEQ ID NO 38
<211> LENGTH: 11
<212> TYPE: PRT
<213> ORGANISM: Mus musculus

<400> SEQUENCE: 38

Pro Tyr Leu Thr Gln Tyr Ala Ile Ile Met Leu
1               5                   10

<210> SEQ ID NO 39
<211> LENGTH: 11
<212> TYPE: PRT
<213> ORGANISM: Mus musculus

<400> SEQUENCE: 39

Pro Asp Leu Thr Gln Tyr Ala Ile Ile Met Leu
1               5                   10

<210> SEQ ID NO 40
<211> LENGTH: 8
<212> TYPE: PRT
<213> ORGANISM: Mus musculus

<400> SEQUENCE: 40

Asp Tyr Val Pro Met Glu Gln Pro
1               5

<210> SEQ ID NO 41
<211> LENGTH: 8
<212> TYPE: PRT
<213> ORGANISM: Mus musculus

<400> SEQUENCE: 41

Asp Asp Val Pro Met Glu Gln Pro
1               5

<210> SEQ ID NO 42
<211> LENGTH: 8
<212> TYPE: PRT
<213> ORGANISM: Mus musculus

<400> SEQUENCE: 42

Pro Tyr Leu Thr Gln Tyr Ala Ile
1               5

<210> SEQ ID NO 43
<211> LENGTH: 8
<212> TYPE: PRT
<213> ORGANISM: Mus musculus

<400> SEQUENCE: 43

Pro Asp Leu Thr Gln Tyr Ala Ile
1               5

```
<210> SEQ ID NO 44
<211> LENGTH: 9
<212> TYPE: PRT
<213> ORGANISM: Mus musculus

<400> SEQUENCE: 44

Pro Tyr Leu Thr Gln Tyr Ala Ile Ile
1               5

<210> SEQ ID NO 45
<211> LENGTH: 9
<212> TYPE: PRT
<213> ORGANISM: Mus musculus

<400> SEQUENCE: 45

Pro Asp Leu Thr Gln Tyr Ala Ile Ile
1               5

<210> SEQ ID NO 46
<211> LENGTH: 9
<212> TYPE: PRT
<213> ORGANISM: Mus musculus

<400> SEQUENCE: 46

Asp Tyr Val Pro Met Glu Gln Pro Arg
1               5

<210> SEQ ID NO 47
<211> LENGTH: 9
<212> TYPE: PRT
<213> ORGANISM: Mus musculus

<400> SEQUENCE: 47

Asp Asp Val Pro Met Glu Gln Pro Arg
1               5

<210> SEQ ID NO 48
<211> LENGTH: 10
<212> TYPE: PRT
<213> ORGANISM: Mus musculus

<400> SEQUENCE: 48

Pro Tyr Leu Thr Gln Tyr Ala Ile Ile Met
1               5                   10

<210> SEQ ID NO 49
<211> LENGTH: 10
<212> TYPE: PRT
<213> ORGANISM: Mus musculus

<400> SEQUENCE: 49

Pro Asp Leu Thr Gln Tyr Ala Ile Ile Met
1               5                   10

<210> SEQ ID NO 50
<211> LENGTH: 10
<212> TYPE: PRT
<213> ORGANISM: Mus musculus

<400> SEQUENCE: 50

Asp Tyr Val Pro Met Glu Gln Pro Arg Pro
1               5                   10
```

```
<210> SEQ ID NO 51
<211> LENGTH: 10
<212> TYPE: PRT
<213> ORGANISM: Mus musculus

<400> SEQUENCE: 51

Asp Asp Val Pro Met Glu Gln Pro Arg Pro
1               5                   10

<210> SEQ ID NO 52
<211> LENGTH: 11
<212> TYPE: PRT
<213> ORGANISM: Mus musculus

<400> SEQUENCE: 52

Asp Tyr Val Pro Met Glu Gln Pro Arg Pro Pro
1               5                   10

<210> SEQ ID NO 53
<211> LENGTH: 11
<212> TYPE: PRT
<213> ORGANISM: Mus musculus

<400> SEQUENCE: 53

Asp Asp Val Pro Met Glu Gln Pro Arg Pro Pro
1               5                   10

<210> SEQ ID NO 54
<211> LENGTH: 9
<212> TYPE: PRT
<213> ORGANISM: Mus musculus

<400> SEQUENCE: 54

Ser Glu Asp Lys Ile Lys Ala Ile Leu
1               5

<210> SEQ ID NO 55
<211> LENGTH: 9
<212> TYPE: PRT
<213> ORGANISM: Mus musculus

<400> SEQUENCE: 55

Ser Glu Asp Lys Ile Lys Ala Ile Pro
1               5

<210> SEQ ID NO 56
<211> LENGTH: 8
<212> TYPE: PRT
<213> ORGANISM: Mus musculus

<400> SEQUENCE: 56

Leu Lys Ser Glu Glu Lys Thr Leu
1               5

<210> SEQ ID NO 57
<211> LENGTH: 8
<212> TYPE: PRT
<213> ORGANISM: Mus musculus

<400> SEQUENCE: 57

Leu Lys Ser Glu Glu Lys Thr Pro
1               5

<210> SEQ ID NO 58
<211> LENGTH: 11
```

```
<212> TYPE: PRT
<213> ORGANISM: Mus musculus

<400> SEQUENCE: 58

Lys Pro Ala Leu Lys Ser Glu Glu Lys Thr Leu
1               5                   10

<210> SEQ ID NO 59
<211> LENGTH: 11
<212> TYPE: PRT
<213> ORGANISM: Mus musculus

<400> SEQUENCE: 59

Lys Pro Ala Leu Lys Ser Glu Glu Lys Thr Pro
1               5                   10

<210> SEQ ID NO 60
<211> LENGTH: 10
<212> TYPE: PRT
<213> ORGANISM: Mus musculus

<400> SEQUENCE: 60

Pro Ala Leu Lys Ser Glu Glu Lys Thr Leu
1               5                   10

<210> SEQ ID NO 61
<211> LENGTH: 10
<212> TYPE: PRT
<213> ORGANISM: Mus musculus

<400> SEQUENCE: 61

Pro Ala Leu Lys Ser Glu Glu Lys Thr Pro
1               5                   10

<210> SEQ ID NO 62
<211> LENGTH: 9
<212> TYPE: PRT
<213> ORGANISM: Mus musculus

<400> SEQUENCE: 62

Ala Leu Lys Ser Glu Glu Lys Thr Leu
1               5

<210> SEQ ID NO 63
<211> LENGTH: 9
<212> TYPE: PRT
<213> ORGANISM: Mus musculus

<400> SEQUENCE: 63

Ala Leu Lys Ser Glu Glu Lys Thr Pro
1               5

<210> SEQ ID NO 64
<211> LENGTH: 11
<212> TYPE: PRT
<213> ORGANISM: Mus musculus

<400> SEQUENCE: 64

Ser Trp Ser Ser Arg Arg Ser Leu Leu Gly Leu
1               5                   10

<210> SEQ ID NO 65
<211> LENGTH: 11
<212> TYPE: PRT
<213> ORGANISM: Mus musculus
```

```
<400> SEQUENCE: 65

Ser Trp Ser Ser Arg Arg Ser Leu Leu Gly Arg
1               5                   10

<210> SEQ ID NO 66
<211> LENGTH: 10
<212> TYPE: PRT
<213> ORGANISM: Mus musculus

<400> SEQUENCE: 66

Gly Phe His Gly Cys Ile His Glu Val Leu
1               5                   10

<210> SEQ ID NO 67
<211> LENGTH: 10
<212> TYPE: PRT
<213> ORGANISM: Mus musculus

<400> SEQUENCE: 67

Gly Phe His Gly Cys Ile His Glu Val Arg
1               5                   10

<210> SEQ ID NO 68
<211> LENGTH: 9
<212> TYPE: PRT
<213> ORGANISM: Mus musculus

<400> SEQUENCE: 68

Gln Val Phe Pro Gly Leu Met Glu Leu
1               5

<210> SEQ ID NO 69
<211> LENGTH: 9
<212> TYPE: PRT
<213> ORGANISM: Mus musculus

<400> SEQUENCE: 69

Gln Val Phe Pro Gly Leu Met Glu Arg
1               5

<210> SEQ ID NO 70
<211> LENGTH: 11
<212> TYPE: PRT
<213> ORGANISM: Mus musculus

<400> SEQUENCE: 70

Thr Thr Thr Pro Gly Gly Arg Pro Pro Tyr Leu
1               5                   10

<210> SEQ ID NO 71
<211> LENGTH: 11
<212> TYPE: PRT
<213> ORGANISM: Mus musculus

<400> SEQUENCE: 71

Thr Thr Thr Pro Gly Gly Arg Pro Pro Tyr Arg
1               5                   10

<210> SEQ ID NO 72
<211> LENGTH: 8
<212> TYPE: PRT
<213> ORGANISM: Mus musculus

<400> SEQUENCE: 72
```

```
Val Phe Pro Gly Leu Met Glu Leu
1               5
```

<210> SEQ ID NO 73
<211> LENGTH: 8
<212> TYPE: PRT
<213> ORGANISM: Mus musculus

<400> SEQUENCE: 73

```
Val Phe Pro Gly Leu Met Glu Arg
1               5
```

<210> SEQ ID NO 74
<211> LENGTH: 10
<212> TYPE: PRT
<213> ORGANISM: Mus musculus

<400> SEQUENCE: 74

```
Glu Leu Gln Gly Leu Leu Glu Asp Glu Leu
1               5                   10
```

<210> SEQ ID NO 75
<211> LENGTH: 10
<212> TYPE: PRT
<213> ORGANISM: Mus musculus

<400> SEQUENCE: 75

```
Glu Leu Gln Gly Leu Leu Glu Asp Glu Arg
1               5                   10
```

<210> SEQ ID NO 76
<211> LENGTH: 11
<212> TYPE: PRT
<213> ORGANISM: Mus musculus

<400> SEQUENCE: 76

```
Lys Leu Gln Arg Gln Tyr Arg Ser Pro Arg Leu
1               5                   10
```

<210> SEQ ID NO 77
<211> LENGTH: 11
<212> TYPE: PRT
<213> ORGANISM: Mus musculus

<400> SEQUENCE: 77

```
Lys Leu Gln Arg Gln Tyr Arg Ser Pro Arg Arg
1               5                   10
```

<210> SEQ ID NO 78
<211> LENGTH: 9
<212> TYPE: PRT
<213> ORGANISM: Mus musculus

<400> SEQUENCE: 78

```
Ser Tyr Met Leu Gln Ala Leu Cys Ile
1               5
```

<210> SEQ ID NO 79
<211> LENGTH: 9
<212> TYPE: PRT
<213> ORGANISM: Mus musculus

<400> SEQUENCE: 79

```
Leu Asp Met Leu Gln Ala Leu Cys Ile
```

<210> SEQ ID NO 80
<211> LENGTH: 10
<212> TYPE: PRT
<213> ORGANISM: Mus musculus

<400> SEQUENCE: 80

Ala Tyr Ile Leu Ala Ala Leu Thr Lys Leu
1               5                   10

<210> SEQ ID NO 81
<211> LENGTH: 10
<212> TYPE: PRT
<213> ORGANISM: Mus musculus

<400> SEQUENCE: 81

Ala Asp Ile Leu Ala Ala Leu Thr Lys Leu
1               5                   10

<210> SEQ ID NO 82
<211> LENGTH: 10
<212> TYPE: PRT
<213> ORGANISM: Mus musculus

<400> SEQUENCE: 82

Pro Tyr Leu Val Leu Lys Phe Gly Pro Val
1               5                   10

<210> SEQ ID NO 83
<211> LENGTH: 10
<212> TYPE: PRT
<213> ORGANISM: Mus musculus

<400> SEQUENCE: 83

Pro Asp Leu Val Leu Lys Phe Gly Pro Val
1               5                   10

<210> SEQ ID NO 84
<211> LENGTH: 10
<212> TYPE: PRT
<213> ORGANISM: Mus musculus

<400> SEQUENCE: 84

Leu Tyr Glu Ala Gly Val Thr Asp Glu Val
1               5                   10

<210> SEQ ID NO 85
<211> LENGTH: 10
<212> TYPE: PRT
<213> ORGANISM: Mus musculus

<400> SEQUENCE: 85

Leu Asp Glu Ala Gly Val Thr Asp Glu Val
1               5                   10

<210> SEQ ID NO 86
<211> LENGTH: 8
<212> TYPE: PRT
<213> ORGANISM: Mus musculus

<400> SEQUENCE: 86

His Tyr Leu Gln Gly Ser Asn Ala
1               5

```
<210> SEQ ID NO 87
<211> LENGTH: 8
<212> TYPE: PRT
<213> ORGANISM: Mus musculus

<400> SEQUENCE: 87

His Asp Leu Gln Gly Ser Asn Ala
1               5

<210> SEQ ID NO 88
<211> LENGTH: 9
<212> TYPE: PRT
<213> ORGANISM: Mus musculus

<400> SEQUENCE: 88

Leu Tyr His Thr Arg Pro Thr Ala Leu
1               5

<210> SEQ ID NO 89
<211> LENGTH: 9
<212> TYPE: PRT
<213> ORGANISM: Mus musculus

<400> SEQUENCE: 89

Leu Asp His Thr Arg Pro Thr Ala Leu
1               5

<210> SEQ ID NO 90
<211> LENGTH: 11
<212> TYPE: PRT
<213> ORGANISM: Mus musculus

<400> SEQUENCE: 90

Ile Tyr Gly Val Val Ala Arg Asn Arg Ala Leu
1               5                   10

<210> SEQ ID NO 91
<211> LENGTH: 11
<212> TYPE: PRT
<213> ORGANISM: Mus musculus

<400> SEQUENCE: 91

Ile Asp Gly Val Val Ala Arg Asn Arg Ala Leu
1               5                   10

<210> SEQ ID NO 92
<211> LENGTH: 9
<212> TYPE: PRT
<213> ORGANISM: Mus musculus

<400> SEQUENCE: 92

Ala Tyr Ala Lys Gln Phe Ala Ala Ile
1               5

<210> SEQ ID NO 93
<211> LENGTH: 9
<212> TYPE: PRT
<213> ORGANISM: Mus musculus

<400> SEQUENCE: 93

Ala Asp Ala Lys Gln Phe Ala Ala Ile
1               5

<210> SEQ ID NO 94
```

```
<211> LENGTH: 10
<212> TYPE: PRT
<213> ORGANISM: Mus musculus

<400> SEQUENCE: 94

Ser Tyr Cys Glu Pro Ala Leu Asn Gln Ala
1               5                   10

<210> SEQ ID NO 95
<211> LENGTH: 10
<212> TYPE: PRT
<213> ORGANISM: Mus musculus

<400> SEQUENCE: 95

Ser Asp Cys Glu Pro Ala Leu Asn Gln Ala
1               5                   10

<210> SEQ ID NO 96
<211> LENGTH: 11
<212> TYPE: PRT
<213> ORGANISM: Mus musculus

<400> SEQUENCE: 96

Val Tyr Leu Thr Cys Arg Leu Glu Lys Pro Ala
1               5                   10

<210> SEQ ID NO 97
<211> LENGTH: 11
<212> TYPE: PRT
<213> ORGANISM: Mus musculus

<400> SEQUENCE: 97

Val Asp Leu Thr Cys Arg Leu Glu Lys Pro Ala
1               5                   10

<210> SEQ ID NO 98
<211> LENGTH: 9
<212> TYPE: PRT
<213> ORGANISM: Mus musculus

<400> SEQUENCE: 98

Lys Tyr Met Ser Met Leu Glu Glu Arg
1               5

<210> SEQ ID NO 99
<211> LENGTH: 9
<212> TYPE: PRT
<213> ORGANISM: Mus musculus

<400> SEQUENCE: 99

Lys Asp Met Ser Met Leu Glu Glu Arg
1               5

<210> SEQ ID NO 100
<211> LENGTH: 10
<212> TYPE: PRT
<213> ORGANISM: Mus musculus

<400> SEQUENCE: 100

Pro Tyr Lys Arg Leu Lys Ala Glu Pro Ala
1               5                   10

<210> SEQ ID NO 101
<211> LENGTH: 10
<212> TYPE: PRT
```

<213> ORGANISM: Mus musculus

<400> SEQUENCE: 101

Pro Asp Lys Arg Leu Lys Ala Glu Pro Ala
1               5                   10

<210> SEQ ID NO 102
<211> LENGTH: 10
<212> TYPE: PRT
<213> ORGANISM: Mus musculus

<400> SEQUENCE: 102

Asp Tyr Ile Ile Glu Phe Ala His Arg Val
1               5                   10

<210> SEQ ID NO 103
<211> LENGTH: 10
<212> TYPE: PRT
<213> ORGANISM: Mus musculus

<400> SEQUENCE: 103

Asp Asp Ile Ile Glu Phe Ala His Arg Val
1               5                   10

<210> SEQ ID NO 104
<211> LENGTH: 9
<212> TYPE: PRT
<213> ORGANISM: Mus musculus

<400> SEQUENCE: 104

Gly Tyr Ser Val Leu His Leu Ala Ile
1               5

<210> SEQ ID NO 105
<211> LENGTH: 9
<212> TYPE: PRT
<213> ORGANISM: Mus musculus

<400> SEQUENCE: 105

Gly Asp Ser Val Leu His Leu Ala Ile
1               5

<210> SEQ ID NO 106
<211> LENGTH: 10
<212> TYPE: PRT
<213> ORGANISM: Mus musculus

<400> SEQUENCE: 106

Ile Tyr Gly Val Val Ala Arg Asn Arg Ala
1               5                   10

<210> SEQ ID NO 107
<211> LENGTH: 10
<212> TYPE: PRT
<213> ORGANISM: Mus musculus

<400> SEQUENCE: 107

Ile Asp Gly Val Val Ala Arg Asn Arg Ala
1               5                   10

<210> SEQ ID NO 108
<211> LENGTH: 11
<212> TYPE: PRT
<213> ORGANISM: Mus musculus

```
<400> SEQUENCE: 108

Leu Tyr Tyr Glu Arg Ile His Lys Lys Met Leu
1               5                   10

<210> SEQ ID NO 109
<211> LENGTH: 11
<212> TYPE: PRT
<213> ORGANISM: Mus musculus

<400> SEQUENCE: 109

Leu Asp Tyr Glu Arg Ile His Lys Lys Met Leu
1               5                   10

<210> SEQ ID NO 110
<211> LENGTH: 10
<212> TYPE: PRT
<213> ORGANISM: Mus musculus

<400> SEQUENCE: 110

Ser Tyr Arg Leu Pro Ser Ser Arg Lys Lys
1               5                   10

<210> SEQ ID NO 111
<211> LENGTH: 10
<212> TYPE: PRT
<213> ORGANISM: Mus musculus

<400> SEQUENCE: 111

Ser Asp Arg Leu Pro Ser Ser Arg Lys Lys
1               5                   10

<210> SEQ ID NO 112
<211> LENGTH: 9
<212> TYPE: PRT
<213> ORGANISM: Mus musculus

<400> SEQUENCE: 112

Leu Tyr Val Ser Lys Leu Asn Gly Pro
1               5

<210> SEQ ID NO 113
<211> LENGTH: 9
<212> TYPE: PRT
<213> ORGANISM: Mus musculus

<400> SEQUENCE: 113

Leu Asp Val Ser Lys Leu Asn Gly Pro
1               5

<210> SEQ ID NO 114
<211> LENGTH: 9
<212> TYPE: PRT
<213> ORGANISM: Mus musculus

<400> SEQUENCE: 114

Leu Tyr Glu Ala Gly Val Thr Asp Glu
1               5

<210> SEQ ID NO 115
<211> LENGTH: 9
<212> TYPE: PRT
<213> ORGANISM: Mus musculus

<400> SEQUENCE: 115
```

```
Leu Asp Glu Ala Gly Val Thr Asp Glu
1               5
```

<210> SEQ ID NO 116
<211> LENGTH: 8
<212> TYPE: PRT
<213> ORGANISM: Mus musculus

<400> SEQUENCE: 116

```
Leu Tyr Asp Val Asp Ala Ala Phe
1               5
```

<210> SEQ ID NO 117
<211> LENGTH: 8
<212> TYPE: PRT
<213> ORGANISM: Mus musculus

<400> SEQUENCE: 117

```
Leu Asp Asp Val Asp Ala Ala Phe
1               5
```

<210> SEQ ID NO 118
<211> LENGTH: 8
<212> TYPE: PRT
<213> ORGANISM: Mus musculus

<400> SEQUENCE: 118

```
Glu Tyr Leu Asp Leu Gln Thr Gln
1               5
```

<210> SEQ ID NO 119
<211> LENGTH: 8
<212> TYPE: PRT
<213> ORGANISM: Mus musculus

<400> SEQUENCE: 119

```
Glu Asp Leu Asp Leu Gln Thr Gln
1               5
```

<210> SEQ ID NO 120
<211> LENGTH: 11
<212> TYPE: PRT
<213> ORGANISM: Mus musculus

<400> SEQUENCE: 120

```
Ala Tyr Ile Leu Ala Ala Leu Thr Lys Leu Gln
1               5                   10
```

<210> SEQ ID NO 121
<211> LENGTH: 11
<212> TYPE: PRT
<213> ORGANISM: Mus musculus

<400> SEQUENCE: 121

```
Ala Asp Ile Leu Ala Ala Leu Thr Lys Leu Gln
1               5                   10
```

<210> SEQ ID NO 122
<211> LENGTH: 11
<212> TYPE: PRT
<213> ORGANISM: Mus musculus

<400> SEQUENCE: 122

```
Ala Tyr Ile Leu Ala Ala Leu Thr Lys Leu Gln
1               5                   10
```

```
<210> SEQ ID NO 123
<211> LENGTH: 11
<212> TYPE: PRT
<213> ORGANISM: Mus musculus

<400> SEQUENCE: 123

Ala Asp Ile Leu Ala Ala Leu Thr Lys Leu Gln
1               5                   10

<210> SEQ ID NO 124
<211> LENGTH: 8
<212> TYPE: PRT
<213> ORGANISM: Mus musculus

<400> SEQUENCE: 124

Ala Tyr Ala Lys Gln Phe Ala Ala
1               5

<210> SEQ ID NO 125
<211> LENGTH: 8
<212> TYPE: PRT
<213> ORGANISM: Mus musculus

<400> SEQUENCE: 125

Ala Asp Ala Lys Gln Phe Ala Ala
1               5

<210> SEQ ID NO 126
<211> LENGTH: 9
<212> TYPE: PRT
<213> ORGANISM: Mus musculus

<400> SEQUENCE: 126

Ala Tyr Arg Leu Glu Gly Asp Arg Ser
1               5

<210> SEQ ID NO 127
<211> LENGTH: 9
<212> TYPE: PRT
<213> ORGANISM: Mus musculus

<400> SEQUENCE: 127

Ala Asp Arg Leu Glu Gly Asp Arg Ser
1               5

<210> SEQ ID NO 128
<211> LENGTH: 10
<212> TYPE: PRT
<213> ORGANISM: Artificial Sequence
<220> FEATURE:
<223> OTHER INFORMATION: exemplary mutated sequence

<400> SEQUENCE: 128

Gly Tyr Ser Val Leu His Leu Ala Ile Ile
1               5                   10

<210> SEQ ID NO 129
<211> LENGTH: 10
<212> TYPE: PRT
<213> ORGANISM: Artificial Sequence
```

```
<220> FEATURE:
<223> OTHER INFORMATION: Exemplary non-mutated sequence

<400> SEQUENCE: 129

Gly Asp Ser Val Leu His Leu Ala Ile Ile
1               5                   10
```

IDENTIFICATION OF TUMOR-PROTECTIVE EPITOPES FOR THE TREATMENT OF CANCERS

CROSS-REFERENCE TO RELATED APPLICATIONS

The present application is a 371 of PCT/US2013/062100, filed on Sep. 27, 2013, which claims the benefit of priority to U.S. Provisional Application Ser. No. 61/707,295 filed on Sep. 28, 2012, under the provisions of 35 U.S.C. 119 and the International Convention for the protection of Industrial Property, the contents of which are incorporated herein in their entirety.

FIELD OF THE DISCLOSURE

The present disclosure relates to methods of identifying tumor-specific epitopes, pharmaceutical compositions such as vaccine compositions comprising tumor-specific epitope peptides, and nucleic acid molecules encoding such peptides.

BACKGROUND

Despite profound advances in the understanding the biology of cancer, the treatment of the most common cancers of adults, such as those of the breast, prostate, lung, colon, ovaries, etc., remains far from satisfactory. Without a doubt, there have been major advances; equally without a doubt, a very large medical need remains unmet. Successful treatment of any disease requires a clear understanding of that which is unique about the disease, followed by finding a way to attack the disease at the point of its uniqueness. This principle has been the basis of all major successes in medicine.

Cancers, in contrast to bacterial infections, for example, are not foreign entities; they are derived from our own self. Because of the overwhelming commonality between cancers and our healthy tissues, cancer has been approached by trying to find biological pathways which the cancers use, and which our normal bodies use less, i.e., to aim for selectivity as opposed to specificity. This approach, illustrated by chemotherapy, is the major nonsurgical approach to cancer therapy today. It is somewhat effective, but since the efficacy is not based on specificity but on selectivity, chemotherapy attacks the normal tissues as well, leading to the well-known side effects of the treatment, which also limit its use.

Recent years have seen increasingly sophisticated tools of chemotherapy, but the fundamental problem that chemotherapy is not specific to cancer but only selective for it remains, and thus it has been for several decades.

An exception that proves the rule is imatinib, a treatment for a common adult leukemia. This kind of leukemia, chronic myelogenous leukemia or CML, results from a very specific change in the blood cells. The change is known and it is also known that the change is only in the leukemia cells. The drug imatinib specifically targets this change and is enormously effective against CML. Unfortunately, CML remains a rather unique example where the specificity can be and has been defined; fortunately, it is also a prime example of the fact that the definition of specificity can lead to highly effective cancer therapy.

What is needed are methods of determining the basis of cancer specificity and then applying this specificity to develop successful, non-toxic therapies.

BRIEF SUMMARY

In one aspect, a method of identifying tumor epitopes in a cancer patient, comprises:

sequencing at least a portion of the cancer patient's RNA or DNA in both a healthy tissue and a cancer tissue, to produce a healthy tissue RNA or DNA sequence and a cancer tissue RNA or DNA sequence, comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set, analyzing the difference DNA marker set to produce a tumor-specific epitope set, wherein the tumor-specific epitope set comprises one or more tumor-specific epitopes, providing a numerical score called the Differential Agretopic Index for each epitope in the tumor-specific epitope set, wherein the Differential Agretopic Index or the DAI is calculated by subtracting a score for a normal epitope from a score for the tumor-specific epitope, optionally producing a pharmaceutical composition comprising a pharmaceutically acceptable carrier and one or more tumor-specific epitope peptides, or one or more polynucleotides encoding the one or more tumor-specific epitope peptides, wherein the one or more tumor-specific epitope peptides are selected from the tumor-specific epitope set based on the Differential Agretopic Index, and optionally administering the pharmaceutical composition to the cancer patient.

In specific embodiments, the pharmaceutical compositions optionally further comprise an adjuvant or immune-modulating agent.

In another aspect, included herein are pharmaceutical compositions comprising tumor-specific epitope peptides or one or more polypeptides containing the tumor-specific epitopes, or polynucleotides encoding the tumor-specific epitope peptides, wherein the tumor-specific epitope peptides are identified by the above-method; and methods of administering the pharmaceutical compositions to cancer patients.

In yet another aspect, included herein is a pharmaceutical composition comprising a pharmaceutically acceptable carrier and one or more tumor-specific epitope peptides, or one or more polypeptides containing the tumor-specific epitopes, or polynucleotides encoding the one or more tumor-specific peptides, wherein the one or more tumor-specific peptides are from a tumor-specific epitope set, wherein the tumor-specific epitope set does not include epitopes from known cancer-causing pathways, wherein the tumor-specific epitope set is specific to a tumor from a cancer patient.

In a still further aspect, a method of identifying a cancer patient as a candidate for immunotherapy comprises sequencing at least a portion of the cancer patient's RNA or DNA in both a healthy tissue and a cancer tissue, to produce a healthy tissue RNA or DNA sequence and a cancer tissue RNA or DNA sequence, comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set, analyzing the difference DNA marker set to produce a tumor-specific epitope set, wherein the tumor-specific epitope set comprises one or more tumor-specific epitopes, quantifying the percentage of non-synonymous single nucleotide variants in the tumor-specific epitope set, and identifying the cancer patient as a candidate for immunotherapy when less than 65% of the single nucleotide variants in the tumor-specific epitope set are non-synonymous single nucleotide variants.

BRIEF DESCRIPTION OF THE DRAWINGS

Referring now to the drawings wherein like elements are numbered alike in several FIGURES:

FIG. 3 shows representative examples of mutant peptides that elicited no response (Top left panel), tumor-specific (i.e., mutant peptide specific) response (Top right panel), tumor/self-cross-reactive response (Bottom left panel) or non-specific response (Bottom right panel).

FIG. 4 shows representative examples of unmutated counterparts of selected mutant peptides that elicited no response (Left panel), unmutated peptide-specific response (Middle panel), or cross-reactive functional CD8 response (as in FIG. 3) (Right panel).

FIG. 5 shows a summary of T-cell responses induced by mutated peptides from mouse fibrosarcomas Meth A (n=92, absolute numbers) (Top left panel), or CMS5 (n=27, absolute numbers) (middle Panel), or a combination of the two (% of each type of T cell response) (Top right panel). The bottom pie chart shows the % of each type of T cell response elicited by unmutated counterparts of mutated peptides (n=119).

FIGS. 6-8 show the landscape of protective tumor immunity elicited by tumor-specific peptides. Mice were immunized with indicated peptides, challenged with live tumor cells, and tumor growth was monitored as described in Methods. Area under the curve (AUC) for each individual tumor growth curve was calculated and normalized by setting the naive group to a value of 100, shown by a horizontal line in FIGS. 6 and 7. Bars corresponding to peptides that show statistically significant tumor-protective immunogenicity are filled in gray, and indicated by an asterisk (P=between 0.015 and 0.03).

FIG. 6 shows the tumor-protective activity of the mutated epitopes with top NetMHC scores for CMS5 and Meth A (Table 4). The peptides are arranged in order of decreasing activity and not in order of their ranking by NetMHC. The pie charts show the percentage of neoepitopes tested that did not (black) and did (gray) elicit protection from tumor challenge.

FIG. 7 shows the tumor-protective activity of the mutated epitopes with top DAI scores for CMS5 and Meth A (Table 5). The peptides are arranged in order of decreasing activity and not in order of their ranking by DAI. The pie charts show the percentage of neo-epitopes tested that did not (black) and did (gray) elicit protection from tumor challenge.

FIG. 8 shows examples of tumor growth curves in untreated mice (naive) and mice immunized with indicated mutant peptides from CMS5. Each line shows the kinetics of tumor growth in a single mouse.

FIG. 9 shows the tumor-protective immunogenicity of the mutated Tnpo3 in mice that were immunized with mutant Tnpo3 peptide, and after a brief stimulation ex vivo without (no pep) or with WT or mutant Tnpo3 peptides, IFNγ+ CD44+ CD8+ T cells were counted.

FIG. 10 shows the tumor-protective immunogenicity of the mutated Tnpo3 in mice that were immunized with irradiated Meth A cells. Left, six days later, cells from inguinal LNs were stimulated overnight without peptide, irrelevant Prpf31 peptide or Tnpo3 peptide. The % of activated effector CD8+ cells is shown. Right, splenocytes were stimulated with 1 μM of indicated peptides once a week. Irrelevant peptide from Prpf31 was used as a control. Nineteen days after stimulation, cells were tested for the responsiveness to indicated peptides.

Figure 1:
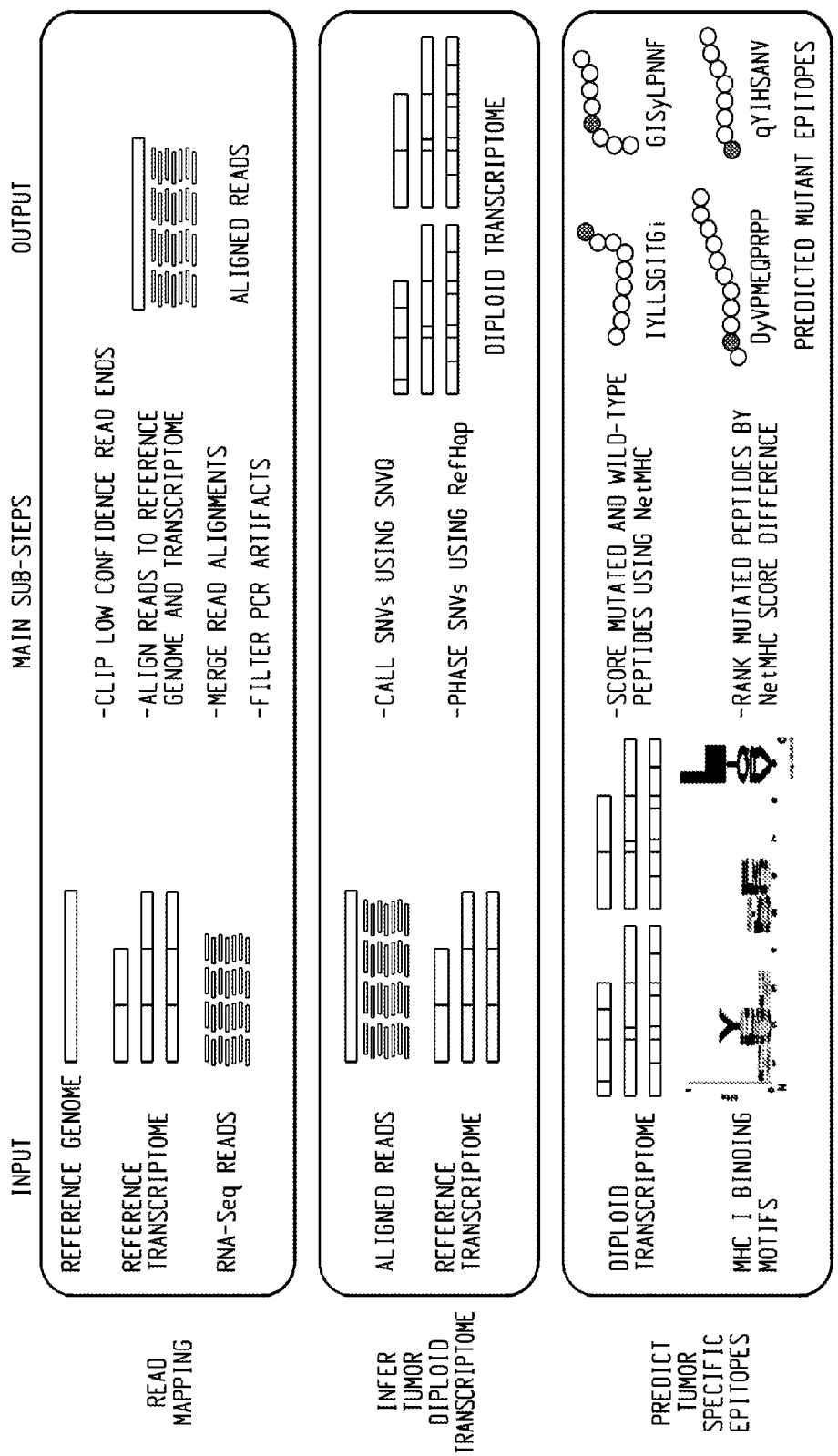
FIG. 1 shows a schematic representation of the Epi-Seq bioinformatics pipeline used to identify tumor specific epitopes from RNA-Seq reads.

The above-described and other features will be appreciated and understood by those skilled in the art from the following detailed description, drawings, and appended claims.

DETAILED DESCRIPTION

The less than complete fidelity of DNA replication is the engine that drives the constant creation of variation (mutations) and natural selection in all cells, including cancer cells. The oncogenic mutations of cancers, and other changes that confer a survival benefit to cancer cells, have drawn most of the attention in the study of cancer genomics thus far. These mutations that are directly related to tumor progression or oncogenesis are called driver mutations. Passenger mutations, in contrast, do not contribute to cancer development, but are rather biologically inert mutations that are carried along to the final tumor. Passenger mutations are far less interesting than driver mutations from a cell biological perspective, since they teach us little about the transformed phenotype of the cells. However, the randomness of passenger mutations makes them unique to each individual tumor. It is important to note that the immune system simply recognizes and reacts to differences regardless of their functional consequences, that is, driver and the passenger mutations are equally significant immunologically and are unique identifiers of particular tumors.

Despite their immunological promise, passenger mutations have not received significant immunological scrutiny, at least in part because they are random and difficult to identify. However, experience with immunotherapy of B cell lymphomas, which harbor individually distinct idiotypes (which are "passenger mutation equivalents") provides experimental and clinical support to the idea that passenger mutations can be used in immunotherapy applications. The availability of techniques such as high throughput DNA sequencing and bioinformatics allows the identification of both driver and passenger mutations, making the passenger mutations available for immunological analysis. In the present disclosure, the passenger mutations of a number of tumors were identified, the vast repertoire of epitopes created by them were dissected, and a range of their immunological anti-tumor activities were observed. As further demonstrated herein, identified passenger mutations and other neoepitopes are not identical in their ability to mediate tumor protection. Thus, in addition to identifying a spectrum of neoepitopes from a tumor, described herein is a new principle and a novel algorithm, the Differential Agretope Index or the DAI, that predicts the tumor-protective properties of mutational neoepitopes. The DAI allows narrowing of the list of epitopes to a small number of tumor-protective epitopes. Also described herein is a new bioinformatic pipeline (Epi-Seq) which made these analyses possible. The methods and compositions described herein will make a quantum leap in our ability to actually implement personalized genomics-driven immunotherapy of human cancer.

Specifically, as shown herein, through a comprehensive genomic, bioinformatic and immunological analysis, hundreds of neoepitopes of mouse and human cancers, previously unidentified by T cell analyses, have been identified. Only a small proportion of neoepitopes elicit protection from tumor growth. Unexpectedly, the predicted affinity of neoepitopes for MHC I has no bearing on protective anti-tumor immunogenicity; instead, the numerical difference of such affinities between the mutated and un-mutated sequences, described herein as the Differential Agretopic Index (DAI), is a significant predictor. Surprisingly, approximately 15% of normal sequences elicit anti-self CD8 responses. These findings shed new light on immunity against self and non-self and provide new opportunities in the development of immunological therapies for cancer.

In one embodiment, a method of identifying tumor epitopes in a cancer patient, comprises:

sequencing at least a portion of the cancer patient's RNA or DNA in both a healthy tissue and a cancer tissue, to produce a healthy tissue RNA or DNA sequence and a cancer tissue RNA or DNA sequence, comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set, analyzing the difference DNA marker set to produce a tumor-specific epitope set, wherein the tumor-specific epitope set comprises one or more tumor-specific epitopes, providing a numerical score called the Differential Agretopic Index for each epitope in the tumor-specific epitope set, wherein the Differential Agretopic Index is calculated by subtracting a score for a normal epitope from a score for the tumor-specific epitope, optionally producing a pharmaceutical composition comprising a pharmaceutically acceptable carrier and one or more tumor-specific epitope peptides or one or more polypeptides containing the tumor-specific epitopes, or polynucleotides encoding the one or more tumor-specific epitope peptides, wherein the tumor-specific epitope peptides are from the tumor-specific epitope set, and a pharmaceutically acceptable carrier based on the Differential Agretopic Index, and further optionally immunizing the cancer patient with the pharmaceutical composition.

The pharmaceutical compositions optionally further comprise an adjuvant or immune-modulating agent.

In one embodiment, sequencing at least a portion of the cancer patient's RNA or DNA in both a healthy tissue and a cancer tissue comprises transcriptome sequencing, genome sequencing, or exome sequencing. Transcriptome sequencing is sequencing the messenger RNA or transcripts from a cell. The transcriptome is the small percentage of the genome (less than 5% in humans) that is transcribed into RNA. Genome sequencing is sequencing the complete DNA sequence of an organism's genome. Exome sequencing is sequencing the protein-encoding parts of the genome. In a specific embodiment, sequencing is transcriptome sequencing, which allows for identification of the mutations that are expressed in tumors.

In another aspect, the depth of sequencing can be varied. In next-generation sequencing, overlapping fragments of the DNA sample of interest are produced and sequenced. The overlapping sequences are then aligned to produce the full set of aligned sequence reads. Depth of sequencing, also called coverage of sequencing, refers to the number of nucleotides contributing to a portion of an assembly. On a genome basis, sequencing depth refers to the number of times each base has been sequenced. For example, a genome sequenced to 30X means that each base in the sequence was covered by 30 sequencing reads. On a nucleotide basis, depth of sequencing refers to the number of sequences that added information about a single nucleotide.

In one aspect RNA or DNA is isolated from tumor and healthy tissue by isolating polyA+RNA from each tissue, preparing cDNA and sequencing the cDNA using standard primers. Such techniques are well-known in the art. Also, sequencing of all or a portion of a patient's genome is well-known in the art. High-throughput DNA sequencing methods are known in the art and include, for example, the HiSeq™2000 system by Illumina® Sequencing Technology, which uses a large parallel sequencing-by-synthesis approach to generate billions of bases of high-quality DNA sequence per run.

In certain embodiments, particular portions of the cancer patient's genome are sequenced, depending on the tumor, for example. In most cases, sequencing the entire genome/transcriptome is preferred; the genome may be sequenced to a shallow depth or a deep depth, allowing coverage or less or more portions of the genome/transcriptome.

In a specific embodiment, analyzing the difference DNA or RNA marker set to produce a tumor-specific epitope set comprises using a predictive algorithm that determines the binding of epitope peptides to MHC molecules. Optionally, the tumor-specific epitope set is refined to provide an MHC-restricted tumor-specific epitope set. For example, MHC I-restricted epitopes of the K, D or L alleles can be provided. MHC-restricted epitope sets can be produced by determining binding of a peptide containing the epitope to an MHC-allele-specific peptide. One example of such an algorithm is NetMHC-3.2 which predicts the binding of peptides to a number of different HLA alleles using artificial neural networks (ANNs) and weight matrices.

Specifically, the DNA (or RNA) sequence differences between the healthy and cancer tissues, in combination with a mammal's MHC composition, are analyzed by an epitope predictive algorithm such as NetMHC. This algorithm produces a list of potential tumor-specific epitopes for this individual mammal, and gives each epitope a numerical score. In the current state of the art, a high score implies a good probability of the epitope being able to immunize, and a low (including a negative) score implies a poor probability of the epitope being able to immunize.

The method further comprises providing a numerical score for each epitope in the tumor-specific epitope set or the MHC-restricted tumor-specific epitope set, wherein the numerical score is calculated by subtracting a score for the normal epitope (non-mutated) from a score for the tumor-specific epitope (mutated). The numerical score for the normal epitope is subtracted from the numerical score for the mutant cancer epitope, and a numerical value for the difference is obtained—the Differential Agretopic Index (DAI) for the epitope. The putative epitopes can be ranked on basis of the DAI. In this ranking, broadly speaking, the higher the difference for a given epitope, the higher the probability that immunization with it shall be protective against the tumor. In a specific embodiment, the highest ranked epitopes are used to immunize an individual. Further, the method can comprise ranking the tumor specific-epitope set or the MHC-restricted tumor-specific epitope set by the Differential Agretopic Index for each epitope in the set. In one aspect, the method further comprises using the ranking by Differential Agretopic Index to identify a subset of 10 to 50 top-ranked tumor specific-epitopes. Top-ranked means the epitopes with the most favorable DAI.

As an example, if the mutated DNA in the cancer, at a given site, codes for an amino acid sequence of GYSVL-HLAII (SEQ ID NO. 128), and the corresponding non-mutated sequence in the normal tissue is GDSVLHLAII (SEQ ID NO. 129). The predictive algorithm (NetMHC in this case) gives a numerical score of +7.3 for the cancer sequence and a score of −4.3 for the normal sequence. The DAI is 11.6. This DAI is used to rank this epitope.

In the current state of art, the numerical score of a mutated epitope given by the predictive algorithm such as NetMHC is the major or sole guide for immunization; the higher the score given by such traditional algorithm, the better a peptide is expected to be. In our analysis, this is not a good method of prediction for tumor-protection. Advantageously, by the methods disclosed herein, (a) the traditional algorithms (like NetMHC) for predicting the score for the non-mutated counterpart, and (b) the difference between the mutated and non-mutated epitope, are used as the guide to predict the anti-tumor immunogenicity of a peptide epitope.

In a specific embodiment, analyzing the difference DNA marker set to produce a tumor-specific epitope set is independent of whether one or more tumor-specific epitopes are related to cancer-causing pathways. Prior methods for analyzing the DNA of cancer patients focused on the genetic mechanisms that cause cancer or that drive cancer, while the present approach is agnostic about that issue. The approach described herein is aimed to attack cancer at any point where it is different from the normal, regardless of whether that difference is responsible for causing cancer or not. A major consequence of this difference is that the other approaches rely mostly on deciding which existing (or future) medicines to use for each patient, and not on designing a medicine for each patient. The present method focuses on designing a medicine to treat a particular tumor.

An advantage of the method described herein is the focus on the differences in the DNA sequences that are specific to cancer. In contrast, with a small number of notable exceptions (ras, p53, bcr-abl translocations, etc.), most of the genetic mechanisms that cause cancer are not truly cancer-specific; instead, normal cells under some normal circumstances also use them. Thus, they are cancer-selective, preferably binding cancer cells over normal cells, but are not cancer-specific, binding both cancer cells and normal cells. The approach described herein is focused on epitopes that are cancer-specific. A distinct benefit of using cancer-specific rather than cancer-selective markers is reduced toxicity of the vaccines that are produced. Further advantages include using immune therapy as opposed to drug therapy which allows for the creation of vaccines having specificity for the actual cancer in the patient.

Identifying differences between the healthy tissue RNA or DNA sequence and a cancer tissue RNA or DNA sequence to produce a difference DNA marker set can be done using bioinformatics technologies known in the art. In one embodiment, the initial screen includes all identifiable changes in the cancer patient's genome. Changes include both synonymous changes (which do not change the encoded amino acid) and non-synonymous changes (which change the encoded amino acid). As explained in the examples, immunoediting results in a reduction in the number of non-synonymous mutations compared to the predicted percentage. In one aspect, a change in a DNA marker is a single nucleotide variant (SNV).

As used herein, a tumor epitope or tumor antigen is a peptide antigen that is produced in tumor cells. Many tumor antigens have been identified in humans as well as mice, for example, various abnormal products of ras and p53 are found in a variety of tumors. In addition to the tumor antigens that are commonly found in different types of tumors, the present inventors have recognized that, depending on the tumor size and the degree of genetic instability, human tumors can have tens to hundreds of truly tumor-specific epitopes. As used herein, a tumor-specific epitope is an epitope that is specific for a particular tumor and is not generally recognized as a tumor antigen.

Also included herein are isolated tumor-specific epitope peptides identified by the methods disclosed herein. An "isolated" or "purified" peptide is substantially free of cellular material or other contaminating polypeptide from the cell or tissue source from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Tumor-specific epitope peptides generally have lengths of 7 to 25 amino acids, specifically 8 to 15 amino acids.

The individual peptides identified in the tumor-specific epitope set can be tested for immunogenicity using methods known in the art.

In one embodiment, a peptide corresponding to each tumor-specific epitope is employed. In another embodiment, a polypeptide containing two or more tumor-specific epitopes is employed. One polypeptide containing multiple tumor-specific epitopes optionally separated by non-epitope linkers can be employed. Such polypeptides can be readily designed by one of ordinary skill in the art.

In certain embodiment, instead of tumor-specific peptides, a pharmaceutical composition comprises one or more polynucleotides encoding the peptides. The peptides can all be expressed from the same polynucleotide molecule, or from multiple polynucleotide molecules.

"Polynucleotide" or "nucleic acid sequence" refers to a polymeric form of nucleotides at least 5 bases in length. The nucleotides can be ribonucleotides, deoxyribonucleotides, or modified forms of either nucleotide. Polynucleotides can be inserted into a recombinant expression vector or vectors. The term "recombinant expression vector" refers to a plasmid, virus, or other means known in the art that has been manipulated by insertion or incorporation of the peptide genetic sequence. The term "plasmids" generally is designated herein by a lower case "p" preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The peptide-encoding polynucleotides can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding the peptides. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included.

A pharmaceutical composition (e.g., a vaccine) comprises at least one isolated tumor-specific epitope peptide (or RNA or DNA encoding such epitope peptides) and a pharmaceutically acceptable carrier. Pharmaceutically acceptable excipients include, for example, diluents, preservatives, solubilizers, emulsifiers, and adjuvants. As used herein "pharmaceutically acceptable excipients" are well known to those skilled in the art. In one embodiment, a pharmaceutical composition allows for local delivery of the active ingredient, e.g., delivery directly to the location of a tumor.

In specific embodiment, a pharmaceutical composition comprises 1 to 100 tumor-specific epitope peptides from the tumor-specific epitope set, specifically 3 to 20 tumor-specific epitope peptides from the tumor-specific epitope set. In another embodiment, a pharmaceutical composition comprises a polypeptide containing 1 to 100 tumor-specific epitope peptides from the tumor-specific epitope set, specifically 3 to 20 tumor-specific epitope peptides from the tumor-specific epitope set. In another aspect, a pharmaceutical composition comprises a polynucleotide encoding 1 to 100 tumor-specific epitope peptides from the tumor-specific epitope set, specifically 3 to 20 tumor-specific epitope peptides from the tumor-specific epitope set.

In one embodiment, pharmaceutical compositions suitable for intravenous, intramuscular, subcutaneous, intradermal, nasal, oral, rectal, vaginal, or intraperitoneal administration conveniently comprise sterile aqueous solutions of the active ingredient with solutions which are preferably isotonic with the blood of the recipient. Such formulations can be conveniently prepared by dissolving the peptide in water containing physiologically compatible substances, such as sodium chloride (e.g., 0.1-2.0 M), glycine, and the like, and having a buffered pH compatible with physiological conditions to produce an aqueous solution, and rendering said solution sterile. These can be present in unit or multi-dose containers, for example, sealed ampoules or vials.

Additional pharmaceutical methods can be employed to control the duration of action. Controlled release preparations can be achieved through the use of polymer to complex or absorb the peptides or nucleic acids. The controlled delivery can be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate a protein, peptides and analogs thereof into particles of a polymeric material, such as polyesters, polyamino acids, hydrogels, polylactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

Local administration to the afflicted site can be accomplished through means known in the art, including, but not limited to, topical application, injection, and implantation of a porous device containing cells recombinantly expressing the peptides, implantation of a porous device in which the peptides are contained.

In one embodiment, the tumor-specific peptide or polynucleotides are mixed with the cells of the cancer patient, for example, by mixing or pulsing, and then administering the mixed or pulsed cells to the cancer patient.

In one embodiment, a vaccine composition further comprises an immune-modulating agent. Exemplary immune-modulating agents include TLR ligands such, for example, CpG oligonucleotide DNA (a TLR9 ligand), lipopeptides and lipoproteins (TLR1 and TLR2 ligands), poly I:C and double stranded RNA (TLR3 ligands), lipopolysaccharide (TLR4 ligand), diacyl lipopeptide (TLR6 ligands), imiquimod (a TLR7 ligand), and combinations of TLR ligands. Another exemplary immune-modulating agent is an antibody such as anti-cytotoxic T-lymphocyte antigen-4 antibody (anti-CTLA-4), or an antibody blocking Programmed Death 1 (PD1) or a PD1 ligand.

Combinations of immune-modulating agents are also contemplated. Examples are: combination of the vaccine with a TLR ligand and anti-CTLA4 antibody, or with CpG and an antibody blocking PD1.

In one embodiment a pharmaceutical composition comprises one or more tumor-specific epitope peptides from a tumor-specific epitope set and a pharmaceutically acceptable carrier, wherein the tumor-specific epitope set does not include known cancer-causing pathways, wherein the tumor-specific epitope set is specific to a tumor from a cancer patient. As used herein, a tumor-specific epitope set is a group of epitopes identified by comparing tumor DNA to normal tissue DNA in the cancer patient, and using the DAI algorithm.

As used herein, a patient is a mammal, such as a mouse or a human, specifically a human patient.

The compositions and methods described herein are applicable to all cancers including solid tumor cancers, e.g., those of the breast, prostate, ovaries, lungs and brain, and liquid cancers such as leukemias and lymphomas.

The methods described herein can be further combined with additional cancer therapies such as radiation therapy, chemotherapy, surgery, and combinations thereof.

In another aspect, disclosed herein is a method of selecting a cancer patient for immunotherapy. As explained in Example 2, it was unexpectedly discovered that new primary cancers have a low proportion of single nucleotide variants that encode non-synonymous changes (approximately 78% in long-standing tumor lines and 23-46% in the new primary cancers). Without being held to theory, it is believed that the reduced number of non-synonymous mutations in the new primary cancers is due to the aggressive response of the immune system to new cancers. Patients with new tumors are better candidates for immunotherapy due to the high activity level of the immune system. Thus, the proportion of non-synonymous single nucleotide variants in a tumor can be used to identify candidates for clinical trials to evaluate immunotherapy as well as treatment using immunotherapy.

In one aspect, a method of identifying a cancer patient as a candidate for immunotherapy comprises sequencing at least a portion of the cancer patient's RNA or DNA in both a healthy tissue and a cancer tissue, to produce a healthy tissue RNA or DNA sequence and a cancer tissue RNA or DNA sequence, comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set, analyzing the difference DNA marker set to produce a tumor-specific epitope set, wherein the tumor-specific epitope set comprises one or more tumor-specific epitopes, quantifying the percentage of non-synonymous single nucleotide variants in the tumor-specific epitope set, and identifying the cancer patient as a candidate for immunotherapy when less than 65% of the single nucleotide variants in the tumor-specific epitope set are non-synonymous single nucleotide variants.

In another aspect, the cancer patient is identified as a candidate for immunotherapy when less than 50%, less than 45%, less than 40%, less than 35%, less than 30% or even less than 25% of the single nucleotide variants in the tumor-specific epitope set are non-synonymous single nucleotide variants.

When the patient is identified as a candidate for immunotherapy, the method further comprises providing a numerical score called the Differential Agretopic Index for each epitope in the tumor-specific epitope set, wherein the Differential Agretopic Index is calculated by subtracting a score for a normal epitope from a score for the tumor-specific epitope as described herein. The method also optionally comprises producing a pharmaceutical composition comprising a pharmaceutically acceptable carrier and one or more tumor-specific epitope peptides, or one or more polynucleotides encoding the one or more tumor-specific epitope peptides, wherein the one or more tumor-specific epitope peptides are selected from the tumor-specific epitope set, and optionally administering the pharmaceutical composition to the cancer patient.

The invention is further illustrated by the following non-limiting examples.

EXAMPLES

Materials and Methods

Mice and tumors. The BALB/cJ mice (6-8 week old female) were purchased from the Jackson Laboratory (Bar Harbor, Me.). B10.D2 TRAMP mice were provided by Dr. Adam Adler. Mice were maintained in the virus-free mouse facilities at the University of Connecticut Health Center. Meth A and CMS5 are fibrosarcomas induced by methyl-cholanthrene in BALB/c mice.

Sample Preparation. Samples were prepared using the Illumina® protocol outlined in "Preparing Samples for Sequencing of mRNA" (Part#1004898 Rev. A September 2008). The protocol consists of two parts: cDNA synthesis and paired-end library preparation. First, mRNA was purified from total RNA using magnetic oligo(dT) beads, then fragmented using divalent cations under elevated temperature. cDNA was synthesized from the fragmented mRNA using Superscript® II (Invitrogen™), followed by $2^{nd}$ strand synthesis. cDNA fragment ends were repaired and phosphorylated using Klenow, T4 DNA Polymerase and T4 Polynucleotide Kinase. Next, an 'A' base was added to the 3' end of the blunted fragments, followed by ligation of Illumina® Paired-End adapters via T-A mediated ligation. The ligated products were size selected by gel purification and then PCR amplified using Illumina® Paired-End primers. The library size and concentration were determined using an Agilent Bioanalyzer.

GAII run conditions. The RNA-seq library was seeded onto the flowcell at 8 pM, yielding approximately 282K to 384K clusters per tile. The library was sequenced using 61 cycles of chemistry and imaging.

Analysis of sequencing data. Initial data processing and base calling, including extraction of cluster intensities, was done using RTA (SCS version 2.6 and SCS version 2.61). Sequence quality filtering script was executed in the Illumina® CASAVA software (ver 1.6.0, Illumina®, Hayward, Calif.).

Epi-Seq Bio-informatics pipeline. A high-level representation of the bioinformatics pipeline used for identifying tumor specific epitopes from high throughput mRNA sequencing data (RNA-Seq) is given in FIG. 1. The pipeline starts by mapping RNA-Seq reads against the strain-specific genome sequences downloaded from the Sanger Mouse Genomes Project and a strain-specific haploid transcript library derived from CCDS annotations. We used BALB/c genome/transcriptome sequences for CMS5 and Meth A cell lines and C57BL sequences for the spontaneous prostate tumors generated from B10D2 mice. Reads were mapped using Bowtie with the default seed length of 28, maximum of 2 mismatches in the seed, and maximum sum of phred quality scores at mismatch positions of 125. Following an initial round of mapping, we calculated mismatch statistics for each read position and each sample (data not shown). Based on this analysis, 2 bases from the 5' end and 10 bases from the 3' end were clipped from all aligned reads. The resulting read alignments were merged using the HardMerge algorithm. HardMerge discards reads that align to multiple locations in the genome and/or transcriptome, as well as reads that align uniquely to both, but at discordant locations. To reduce the effect of bias introduced by PCR amplification during library preparation, we replaced multiple reads with alignments starting at the same genomic location with their consensus. The SNVQ algorithm was then used to call single nucleotide variants (SNVs) from the filtered set of aligned reads. SNVQ uses Bayes' rule to call the genotype with the highest probability while taking base quality scores into account. High confidence SNVs were selected by requiring a minimum phred quality score of 50 for each called genotype, a minimum of 3 reads supporting the alternative allele, with at least one read mapping on each strand. Haplotype inference over called SNV genotypes was performed using the RefHap Single Individual Haplotyping algorithm in that uses read evidence to phase blocks of proximal SNVs. Since residual heterozygosity in the inbred mice used in the experiments is predicted to be low, unique heterozygous SNVs were considered to be novel somatic mutations. Homozygous SNVs as well as heterozygous SNVs shared by more than one tumor with the same genome background were assumed to be germ-line mutations and were not used for epitope prediction unless located near a unique heterozygous SNV. For each unique heterozygous SNV, reference and alternative peptide sequences were generated based on the two inferred haplotypes for each CCDS transcript. Generated amino acid sequences were then run through the NetMHC 3.0 epitope prediction program and scored using the Profile Weight Matrix (PWM) algorithm with default detection thresholds.

Binding assays. Binding of peptides to H-2 $K^d$ was determined using quantitative assays based on the inhibition of binding of a radiolabeled standard peptide to purified MHC molecules, essentially as known in the art. Briefly, 0.1 to 1 nM of a radiolabeled known MHC-binding peptide (H-2 consensus motif peptide 1079.03; sequence KFNPMFTYI (SEQ ID NO. 1) was co-incubated at room temperature with varying amounts of unlabeled test peptides, 1-10 nM H-2 $K^d$ molecules purified by affinity chromatography, a cocktail of protease inhibitors and 1 µM human B2-microglubulin (Scripps Laboratories, San Diego, Calif.). After a 2-day incubation, MHC-peptide complexes were captured on LUMITRAC 600 microplates (Greiner Bio-one, Longwood, Fla.) coated with monoclonal antibody SF1-1.1.1. Bound radioactivity was measured using a TopCount® microscintillation counter (Packard Instrument Co., Meriden, Conn.). The concentration of peptide yielding 50% inhibition of the binding of the radiolabeled probe peptide ($IC_{50}$) was then calculated. Peptides were typically tested at six different concentrations covering a 100,000-fold dose range, and in three or more independent assays. Under the conditions utilized, where [label]<[MHC] and $IC_{50}$≥[MHC], the measured IC50 values are reasonable approximations of the KD values.

Foot pad immunization. Peptides (300 µg peptide in 75 µl PBS) were emulsified by vortexing with 75 µl TiterMax® (Sigma-Aldrich®, St. Louis, Mo.) at 2,500 RPM for 30 min. Mice were immunized with 50 µl of emulsion in the foot pad. One week later, popliteal dLNs were harvested for the intracellular IFN-γ assay.

Intracellular IFN-γ assay. Splenocytes or lymphoctes were incubated either with or without 1-10 µg/ml peptide. GolgiPlug™ (BD™ Biosciences, San Jose, Calif.) was added 1 hour later. After incubation of 12 to 16 h at 37° C. with 5% $CO_2$, cells were stained for CD44 (clone IM7), CD4 (clone GK1.5) and CD8 (clone 53-6.7) (BD™ Biosciences, San Jose, Calif.), fixed and permeabilized using the Cytofix/Cytoperm™ kit (BD™ Biosciences, San Jose, Calif.), and stained for intracellular IFN-γ using Phycoerythrin-conjugated anti-mouse IFN-γ (clone XMG1.2, BD™ Biosciences, San Jose, Calif.). Cells were stained with 1 µl antibody/million cells in 50 µl staining buffer (PBS with 1% bovine serum albumin) and incubated for 20 min at 4° C. in the dark, or according to the manufacturer's instructions. Cells were assessed on a FACSCalibur™ flow cytometer (Becton Dickinson, San Jose, Calif.) and results were analyzed using FlowJo software (TreeStar, San Carlos, Calif.). Surface CD44 and intracellular IFN-γ were quantified on gated $CD8^+CD4^-$ cells.

Tumor challenge and representation of tumor growth. BALB/cJ mice were immunized twice weekly with intradermal injections of irradiated peptide-pulsed splenocytes (2000 rad). The mice were shaved the day before tumor challenge. Seven days after the last immunization, 100,000 live Meth A ascites cells, or 200,000 cultured CMS5 cells (viability >98% by trypan blue exclusion) were injected intradermally on the lower right flank of mice. In some experiments, immune-modulatory therapies were combined with immunization. Some mice were injected subcutaneously twice biweekly with 50 µg CpG ODN1826 (Invivo-Gen™, San Diego, Calif.). To target $CD25^+$ cells, 250 µg anti-CD25 mAb (clone PC61, rat IgG1, Monoclonal Antibody Core Facility at MSKCC, New York, N.Y.) was injected intraperitoneally two days before tumor challenge. One hundred microgram of anti-CTLA-4 antibody (clone 9D9, mouse IgG2b, BioXCell, West Lebanon, N.H.) was injected intraperitoneally at seven days before and every three days after tumor challenge. Tumor diameters were measured by calipers twice a week. Mice were sacrificed when tumors ulcerated, reached a maximum diameter of 20 mm or when mice showed any sign of discomfort. AUC as a tool to measure tumor growth has been described in the art. Briefly, AUC was calculated by selecting "Curves & Regression" and then "Area under curve" from the "analyze" tool, using the Prism® 5.0 (GraphPad Software, Inc., La Jolla, Calif.). Grubb's test was used to remove up to one outlier from each group.

Statistical analysis. P-values for group comparisons were calculated using a two-tailed non-parametric Mann-Whitney test, using GraphPad Prism® 5.0 (GraphPad Software, Inc., La Jolla Calif.). For tumor rejection assays, Grubb's test was used to remove up to one outlier from each group. Fisher's Exact test was used to evaluate the correlation between any two parameters.

Example 1: From Transcriptomes to Immunomes

Transcriptomes of six mouse tumors of the d haplotype (CMS5 and Meth A fibrosarcomas of BALB/c mice, and four primary prostate adenocarcinomas of B10.D2 TRAMP mice) were sequenced to varying depths. Transcriptome sequencing was chosen over genome or exome sequencing in order to identify mutations specifically in the genes expressed in the tumors. Broadly speaking, the cDNA sequences obtained were compared with the normal mouse sequences, and single nucleotide variants (SNVs) were identified in each individual tumor (Table 1).

Meth A and CMS5 have been long-standing workhorses for identification of tumor-specific epitopes using T cells and antibodies as probes. Extensive analyses for more than 25 years using immunological probes has yielded only four epitopes in the Meth A, and a single epitope in the CMS5 tumor.

TABLE 2

Mapping SNV, and NetMHC predicted epitope statistics for 1, 2, respectively 3 lanes of Meth A RNA-Seq reads (related to Table 1)

| | Number of RNA-Seq lanes | | |
|---|---|---|---|
| | 1 | 2 | 3 |
| RNA-Seq Reads (Million) | 35.9 | 62.9 | 105.8 |
| Genome Mapped | 75% | 86% | 75% |
| Transcriptome Mapped | 83% | 95% | 83% |
| HardMerge Mapped | 66% | 75% | 65% |

TABLE 1

Single nucleotide variants and predicted epitopes of tumor lines and primary tumors as deduced from transcriptome sequencing and bioinformatic analyses.

| | Mouse Strain | | | | | |
|---|---|---|---|---|---|---|
| | BALB/c | | B10.D2 TRAMP | | | |
| Tumor Type | Meth A | CMS5 | ProCa1 | ProCa2 | ProCa3 | ProCa4 |
| RNA-Seq Reads (Million) | 105.8 | 23.4 | 74.2 | 38.3 | 30.5 | 15.1 |
| Genome Mapped | 75% | 54% | 61% | 56% | 71% | 75% |
| Transcriptome Mapped | 83% | 59% | 44% | 29% | 55% | 69% |
| HardMerge Mapped | 65% | 48% | 39% | 27% | 47% | 57% |
| After PCR Amplification Filter | 18% | 22% | 10% | 6% | 24% | 30% |
| HardMerge and Filtered Mapped Bases (Gb) | 1.15 | 0.24 | 0.35 | 0.11 | 0.35 | 0.22 |
| High-Quality Heterozygous SNVs in CCDS Exons* | 1,528 | 208 | 134 | 18 | 141 | 79 |
| Tumor Specific | 1,504 | 191 | 30 | — | 51 | 15 |
| Non-synonymous | 77.1% | 78.5% | 43.3% | — | 23.5% | 46.7% |
| Missense | 1,096 | 146 | 13 | — | 12 | 7 |
| Nonsense | 63 | 4 | — | — | — | — |
| No-stop | 1 | — | — | — | — | — |
| NetMHC Predicted Epitopes** | 823 | 112 | 10 | — | 1 | 18 |
| H2 $K^d$-restricted | 203 | 15 | — | — | — | 1 |
| H2 $D^d$-restricted | 328 | 58 | 8 | — | — | 10 |
| H2 $L^d$-restricted | 292 | 39 | 2 | — | 1 | 7 |

*The number of mutations identified depends on the sequencing depth. See Table 2 for analysis of the effect of sequencing depth on calling mutations in the Meth A sample.

Figure 2:
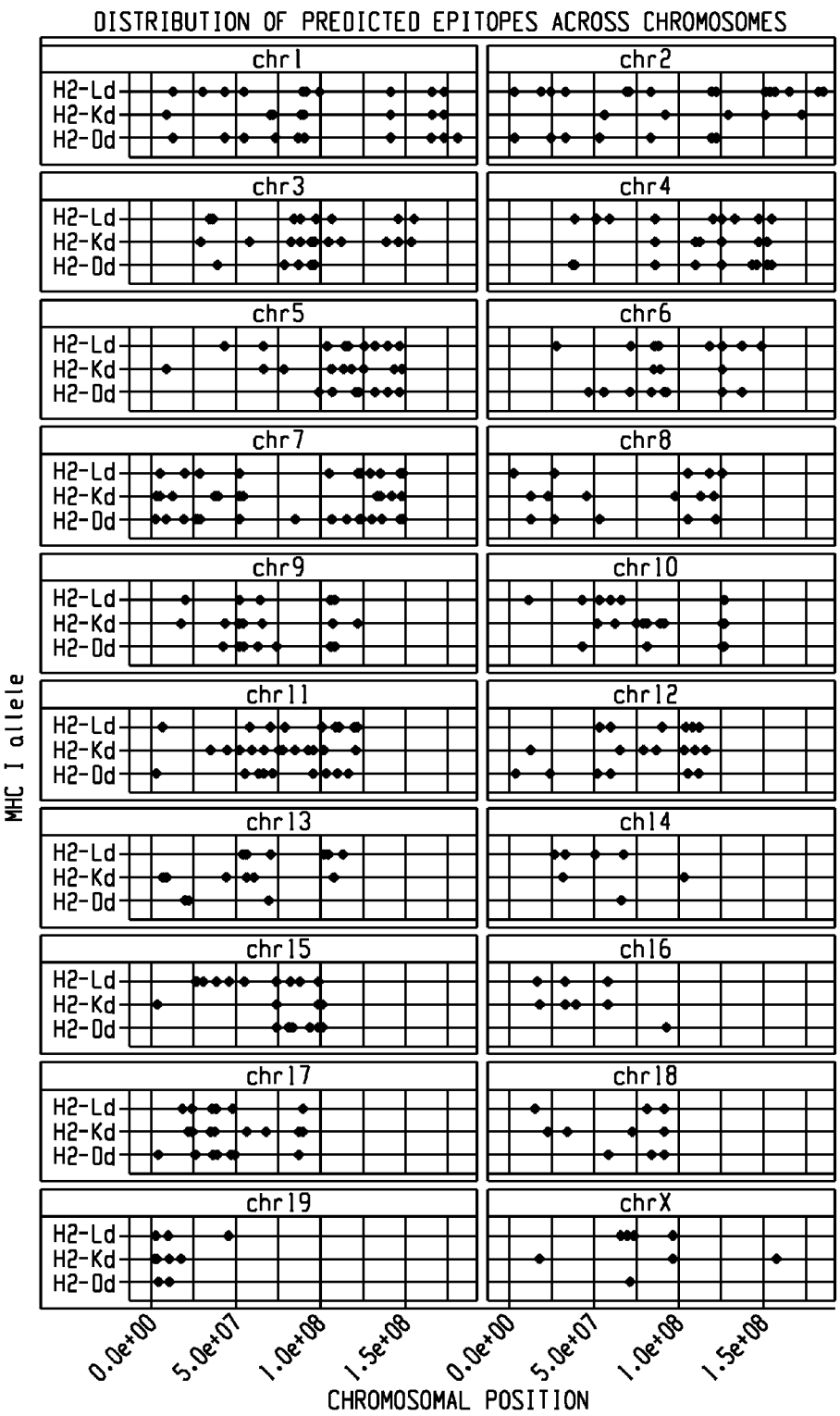
FIG. 2 shows the chromosomal distribution of the MHC I-restricted epitopes of the Meth A sarcoma. The L, K and D-presented epitopes are shown in top, middle and bottom panels, respectively, on each chromosome. For the x-axis, 1.5e+08 is chromosomal position 150,000,000, and 0 is chromosomal position 0. Due to allelic exclusion of gene expression on the X chromosome, the heterozygosity filter used in the Epi-Seq pipeline was not applied to mutations on that chromosome. X chromosome mutations in this figure are predicted using both homozygous and heterozygous mutations.

FIG. 1 and Table 2 show the bioinformatic pipeline and the quality control steps created for this analysis. This pipeline, named the Epi-Seq pipeline, is publicly accessible. The SNVs were analyzed for their potential to generate MHC I-restricted epitopes of the K, D or L alleles using the NetMHC algorithm (total output from this pipeline not shown). Using defined thresholds, this vast number of putative epitopes was reduced to a smaller number (Table 1). By this analysis, the chemically induced tumor lines Meth A and CMS5 harbor 823 and 112 potential epitopes respectively (Table 1); the difference in the number of epitopes identified between these two lines is a reflection of the depth to which their transcriptomes were sequenced. The putative neoepitopes (shown only for the Meth A) are randomly distributed over the entire genome (FIG. 2), with the exception of the X chromosome, which has significantly fewer non-synonymous mutations and fewer epitopes, presumably because of the lower gene density of this chromosome in mammals. It is of interest to point out that the two tumors TABLE 2-continued Mapping SNV, and NetMHC predicted epitope statistics for 1, 2, respectively 3 lanes of Meth A RNA-Seq reads (related to Table 1)

| | Number of RNA-Seq lanes | | |
|---|---|---|---|
| | 1 | 2 | 3 |
| After PCR Amplification Filter | 27% | 24.89% | 18% |
| HardMerge and Filtered Mapped Bases (Gb) | 0.59 | 0.94 | 1.15 |
| High-Quality Heterozygous SNVs in CCDS Exons | 958 | 1,342 | 1,504 |
| Non-synonymous | 75.9% | 76.5% | 77.1% |
| Missense | 691 | 971 | 1,096 |
| Nonsense | 35 | 55 | 63 |
| No-stop | 1 | 1 | 1 |
| NetMHC Predicted Epitopes | 537 | 729 | 823 |
| H2 $K^d$-restricted | 116 | 182 | 203 |

TABLE 2-continued

Mapping SNV, and NetMHC predicted epitope statistics for 1, 2, respectively 3 lanes of Meth A RNA-Seq reads (related to Table 1)

| | Number of RNA-Seq lanes | | |
|---|---|---|---|
| | 1 | 2 | 3 |
| H2 $D^d$-restricted | 222 | 280 | 328 |
| H2 $L^d$-restricted | 199 | 267 | 292 |

In contrast to the Meth A and CMS5 tumor lines of long standing, the number of $K^d$-presented neo-epitopes detected in the four spontaneous prostate cancers is very low (between 0 and 18). The spontaneous prostate cancers are of very recent vintage, the actual age of the tumors being less than 6 months, and the small number of epitopes in these tumors is consistent with the thesis that the neoepitopes are generated as a result of spontaneous mutation rate per cell division.

We have used this bioinformatic pipeline to analyze the newly published list of mutations derived from transcriptome sequencing data of 14 human prostate cancers and normal tissues, and have identified a number of putative epitopes for the most common HLA alleles (Table 3). Interestingly, the human prostate cancers are observed to harbor a relatively small number of neoepitopes, comparable to the numbers seen in the spontaneous tumors of TRAMP mice, even though the human tumors are arguably much older than the mouse tumors. An analysis of exome sequences of several human melanomas and their comparison with corresponding normal sequences through the bioinformatic pipeline reveals hundreds of putative neoepitopes per human melanoma. Several bases of such large differences in the numbers of neoepitopes among human tumor can be imagined and tested.

Example 2: Proportion of Non-Synonymous Mutations, a Likely Indicator of Immuno-Editing A second important distinction between the long-standing tumor lines and the new primary cancers is the proportion of SNVs that encode non-synonymous mutations (which lead to changes in the encoded amino acid) as opposed to synonymous mutations (approximately 78% in the tumor lines and 23-46% in the primary cancers). Based on the degeneracy of the genetic code and frequency of usage of the individual codons, the proportion of non-synonymous mutations in an unselected population of mutations should be about 75%, as indeed seen in the tumor lines CMS5 and Meth A, as well as in eight human cancer lines that are cultured in vitro and are therefore under no immunological selection pressure. The dramatically reduced (23-46%) proportion of non-synonymous mutations in the primary cancers is best explained by the hypothesis that a significant proportion of tumor cells with non-synonymous mutations were eliminated by the immune system. There is strong independent evidence of immuno-editing in the early phase of tumorigenesis. Our data are the first to suggest that the number of non-synonymous passenger mutations as a proportion of the total number of passenger mutations in a tumor is predictive of the status of immuno-editing in that tumor. Analysis of transcriptome sequences of 14 human prostate cancer specimens shows that about 60% of the mutations are non-synonymous, as compared to an expectation of approximately 75% in case of un-edited tumors. This number signifies that while the young prostate tumors of TRAMP mice are undergoing aggressive immunological selection (with 23-47% of the mutations being non-synonymous), the advanced human tumors are perhaps already in the escape phase (with 60% of the mutations being non-synonymous). A similar analysis in human melanomas shows a range of proportions of non-synonymous mutations, from 58% to 72%, suggesting tumors at a range of stages of immuno-editing.

TABLE 3

Summary of the high throughput transcriptome sequencing data and prediction of tumor-specific polymorphisms and epitopes for 14 human prostate cancer samples*

| | Somatic mutations reported in Ren et al. (11) | | | | | | | | | |
|---|---|---|---|---|---|---|---|---|---|---|
| | Synonymous/nonsynonymous in UCSC annotation | | Subset of nonsynonymous mutations within CCDS coding regions | | | | | | | |
| Tumor Sample | Synon- ymous | Non-synon- ymous | Total | Hetero- zygous | Mis- sense | Non- sense | NetMHC predicted epitopes | | | |
| | | | | | | | Total | A1101 | A2402 | A0201 |
| 1T | 7 | 10 | 10 | 10 | 9 | 1 | 9 | 4 | 0 | 5 |
| 2T | 4 | 3 | 2 | 2 | 2 | 0 | 4 | 4 | 0 | 0 |
| 3T | 7 | 4 | 3 | 3 | 3 | 0 | 10 | 5 | 1 | 4 |
| 4T | 5 | 3 | 3 | 3 | 3 | 0 | 2 | 2 | 0 | 0 |
| 5T | 4 | 7 | 7 | 7 | 7 | 0 | 18 | 12 | 2 | 4 |
| 6T | 3 | 5 | 5 | 5 | 4 | 1 | 3 | 1 | 0 | 2 |
| 7T | 2 | 3 | 2 | 2 | 2 | 0 | 2 | 1 | 1 | 0 |
| 8T | 20 | 44 | 40 | 40 | 38 | 2 | 82 | 42 | 7 | 33 |
| 9T | 13 | 22 | 18 | 18 | 16 | 2 | 30 | 13 | 0 | 17 |
| 10T | 20 | 32 | 29 | 29 | 28 | 1 | 36 | 20 | 3 | 13 |
| 11T | 6 | 13 | 9 | 9 | 9 | 0 | 17 | 8 | 2 | 7 |
| 12T | 3 | 11 | 10 | 10 | 10 | 0 | 28 | 13 | 5 | 10 |
| 13T | 2 | 5 | 5 | 5 | 5 | 0 | 9 | 2 | 3 | 4 |
| 14T | 19 | 32 | 29 | 29 | 24 | 5 | 53 | 25 | 8 | 20 |

*Calculated from published mutation data, and using the epitope prediction step of the Epi-Seq pipeline summarized in FIG. 1 to call the epitopes based on the mutation data.

Example 3: Immunogenicity of Neo-Epitopes Identified in Silico

Figure 3:
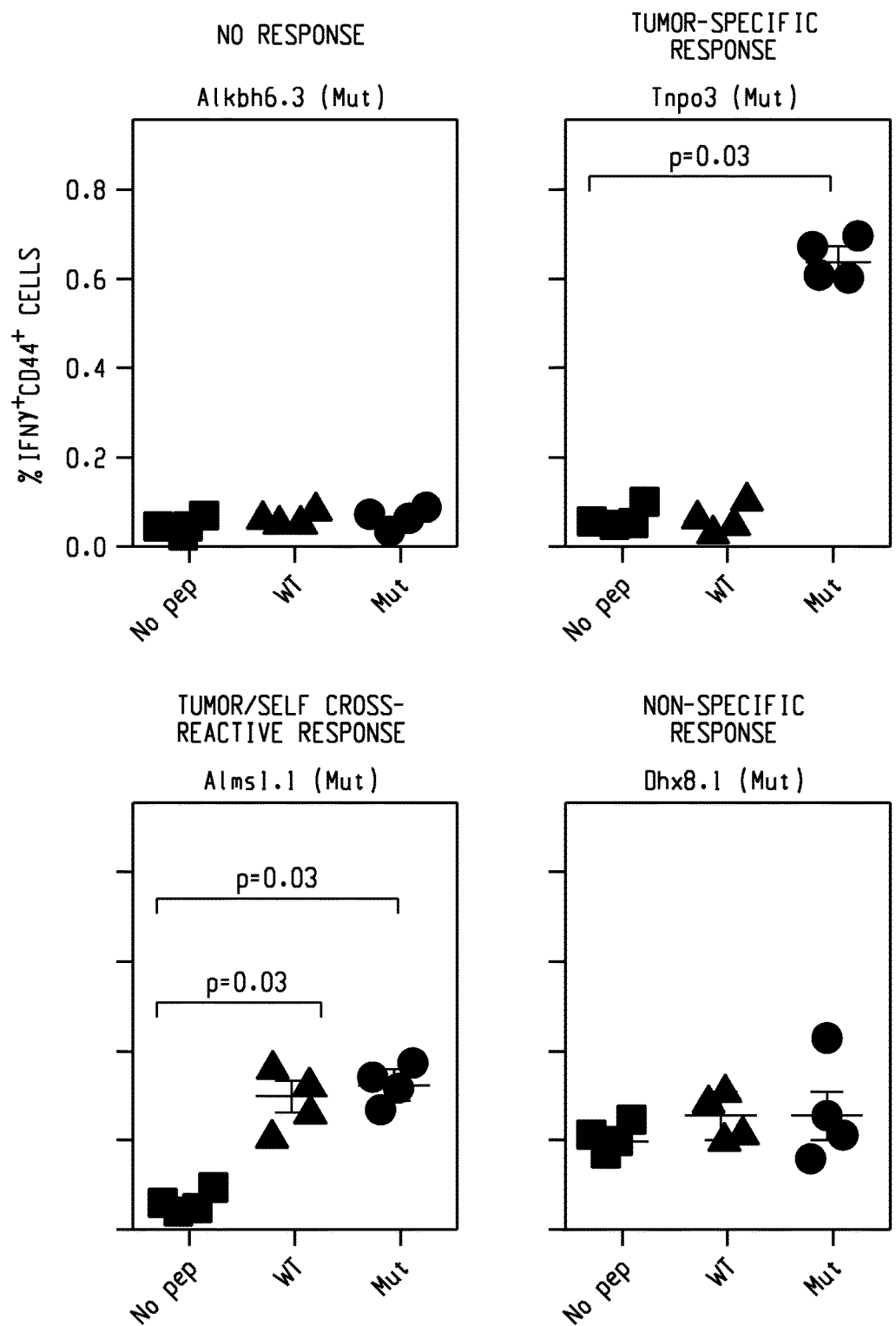
FIGS. 3-5 show the immunogenicity of epitopes generated by point mutations. Mice were immunized in the footpad with indicated peptides. One week later, draining lymph nodes (dLNs) were harvested and their cells were stimulated overnight in vitro without peptides (no pep) or with mutated (Mut) peptides or their unmutated (WT) counterparts. Surface CD44 and intracellular IFN-γ positive cells were counted on 20,000 gated CD8+ cells.
Figure 5:
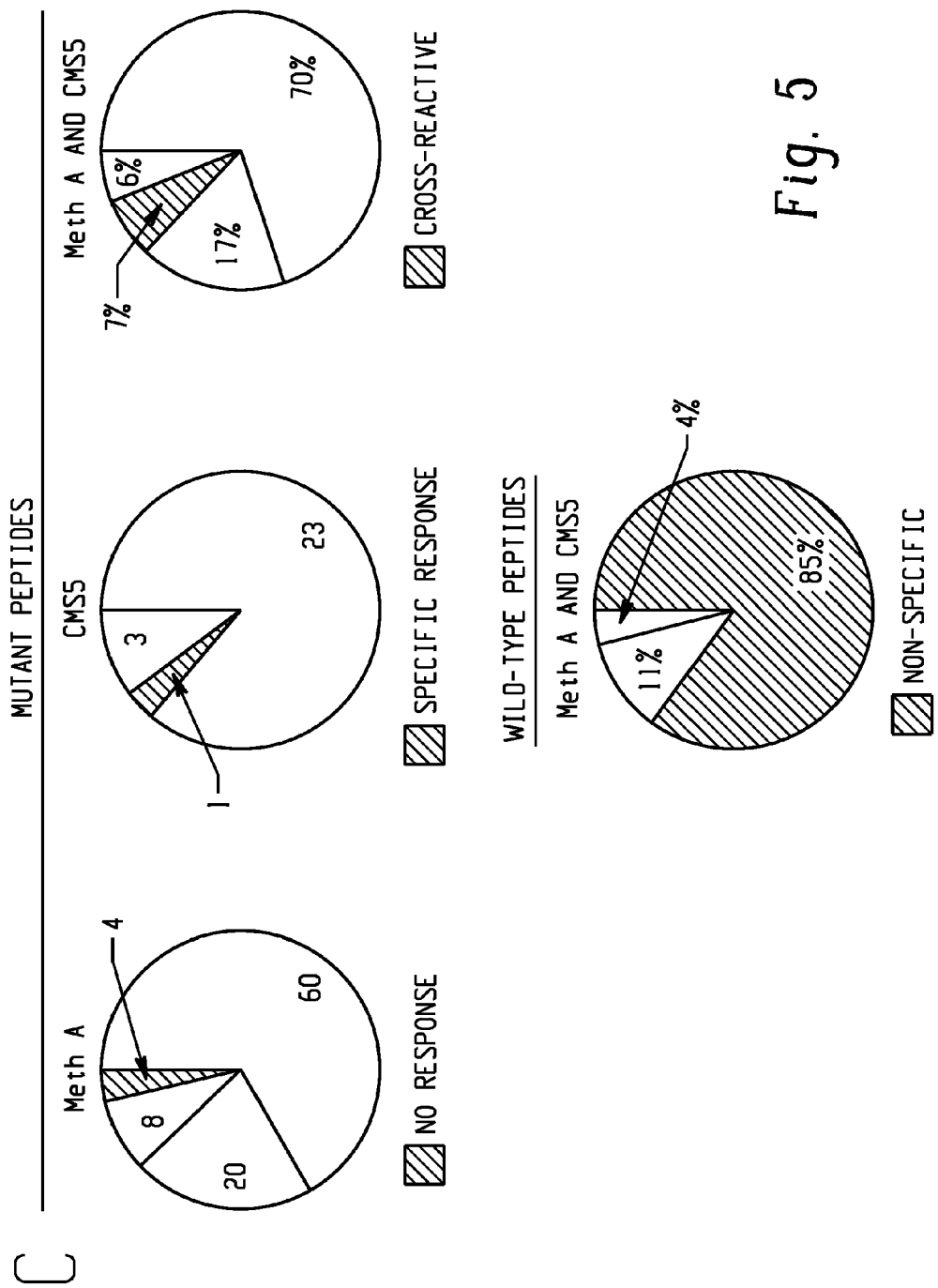

For the sake of focus, attention was directed towards the 218 $K^d$-restricted epitopes (for Meth A and CMS5 combined) from a total list of 935 for all three alleles (Table 1); 119/218 predicted epitopes of CMS5 and Meth A tumors, were selected, and were used to immunize BALB/c mice. The draining lymph nodes (dLNs) of immunized mice were harvested one week after the single immunization, and the cells were stimulated in vitro for 16 h without any added peptide, or the mutant peptide used for immunization, or the corresponding wild type peptide. The CD8+ cells were analyzed for activation (CD44+) and effector function (Interferon γ+). All possible patterns of immune-reactivity were observed (FIG. 3, 5): no immune response (83/119), a mutant peptide-specific, i.e., tumor-specific immune response (21/119), a cross-reactive response between the mutant and corresponding wild type peptides (8/119), and a non-specific response (7/119). All four types of responses were elicited by both tumors (FIG. 5). Surprisingly, a large proportion of putative epitopes (83/119 or 70%) elicited no immune response at all. The affinity of all peptides for $K^d$ was determined experimentally as described in Methods, and a significant correlation was observed between the measured IC50 of $K^d$-peptide interaction and immune response (P=0.003 by Fisher's Exact test).

Figure 4:
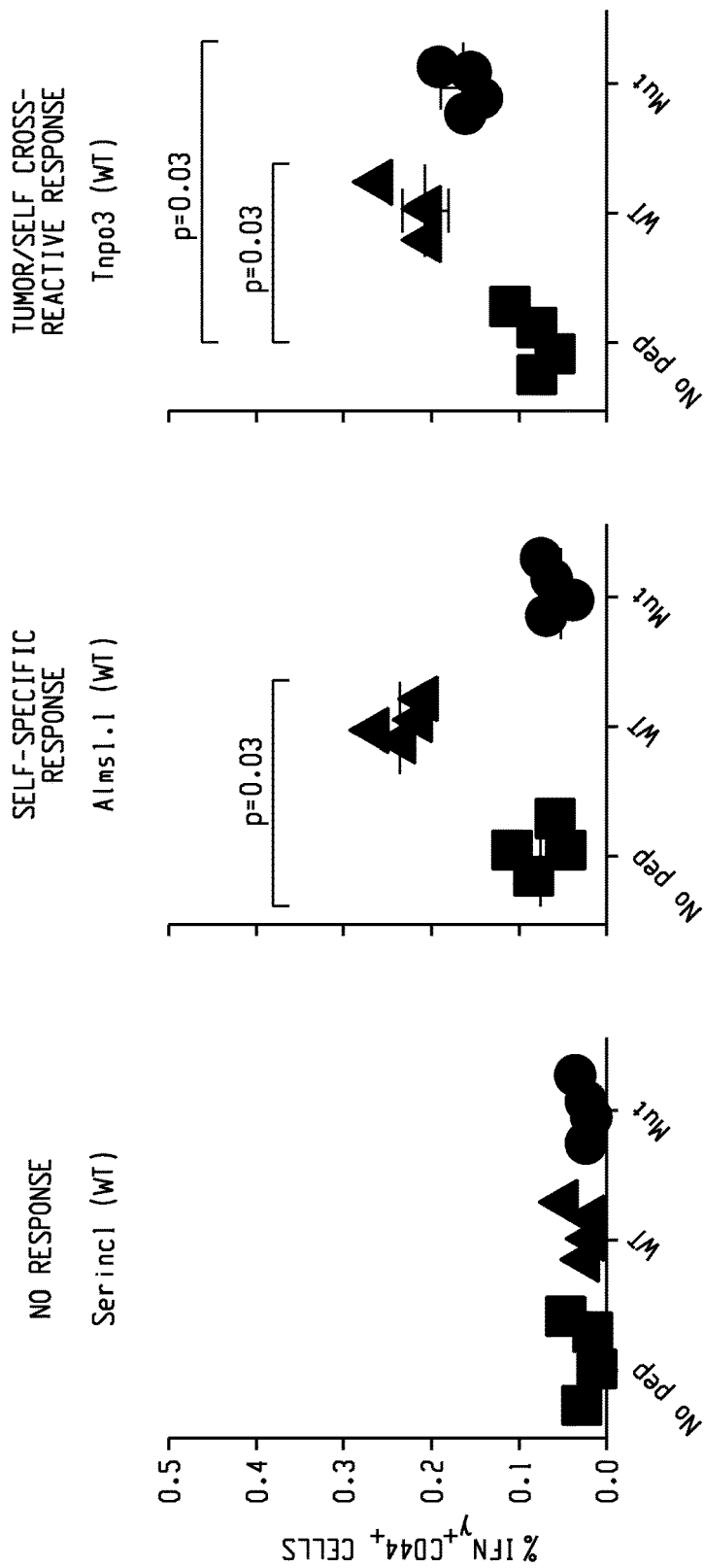

As controls, wild type (unmutated peptides) corresponding to the mutant peptides were used to immunize mice and tested for immune response (FIG. 4, 5). A small but surprisingly significant 15% of peptides tested (n=66) elicited specific responses. Arguably, CD8+ T cells against these self-epitopes did not undergo central deletion; to our knowledge, this is the first experimental testing of a large number of normal sequences having been tested for immunogenicity, and the proportion of self-immunogenic epitopes, albeit small, is significantly larger than may have been expected (although no precise estimates exist). Alternatively, many of the normal sequences selected may represent cryptic epitopes that are never actually presented because of barriers to antigen processing.

In order to determine the extent of antigenic heterogeneity with respect to the neoepitopes identified, Meth A cells were cloned and 30 distinct clones were tested for each of the four SNVs picked at random. Unexpectedly, all but a single SNV was expressed in all the clones; a single SNV was expressed in 29/30 clones tested (data not shown). Without being held to theory, this lack of antigenic heterogeneity is attributed to the relatively shallow depth of sequencing. Turning this idea on its head, it is possible to use a relatively shallow sequencing as a methodology to identify only the broadest antigenic fingerprint of any tumor.

Example 4: Tumor-Protectivity of Putative Neoepitopes

Figure 6:
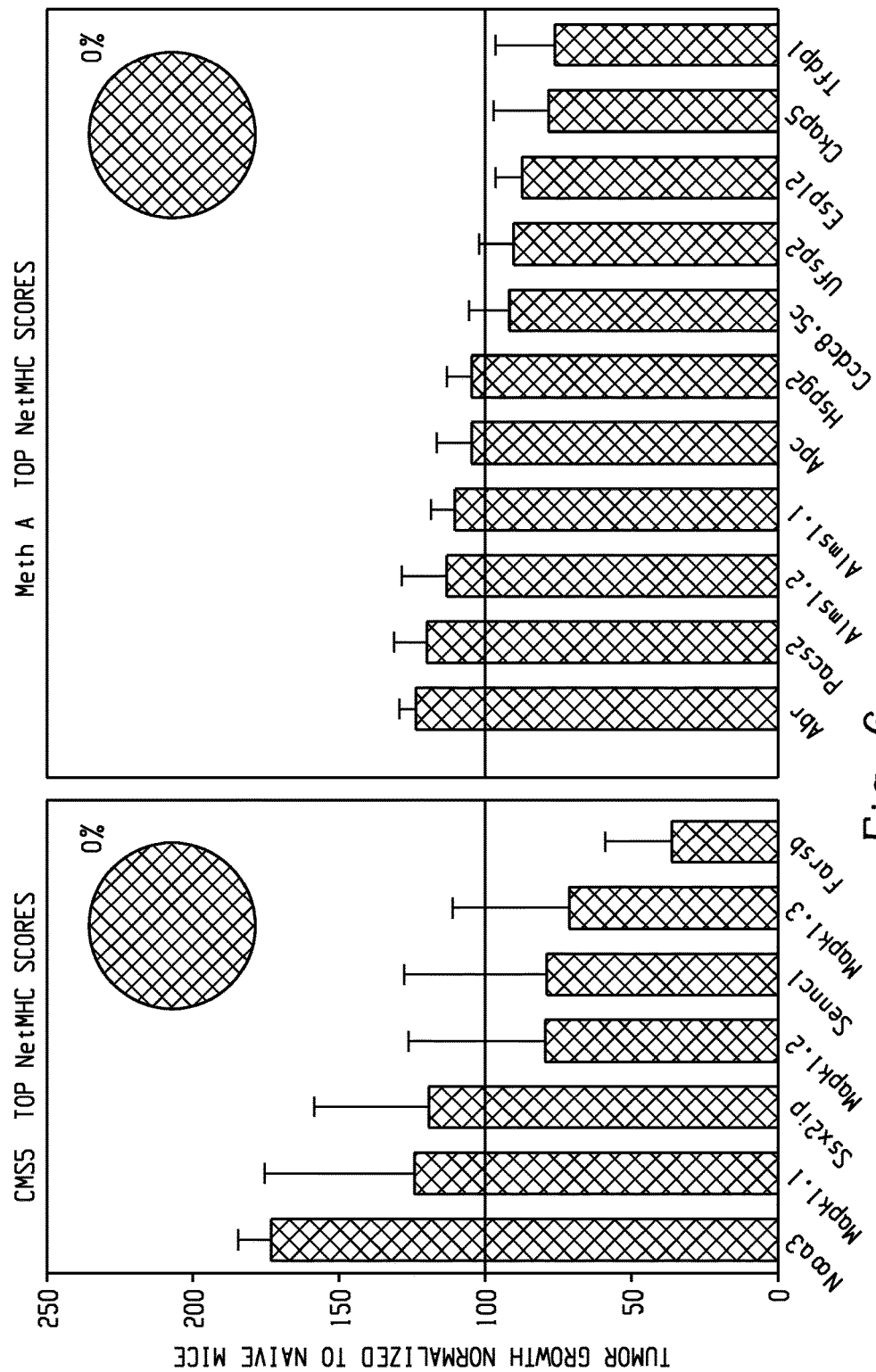

The ability of the predicted epitopes to elicit protective tumor immunity was assessed experimentally. The seven CMS5 epitopes and 11 Meth A epitopes with the highest NetMHC scores (Table 4) were tested. BALB/c mice were immunized twice with the individual peptides (as described in Methods) and were challenged with the appropriate tumor one week after the last immunization. FIG. 6 shows that none of the neo-epitopes (0/18 or 0%) elicited protection from tumor growth, even though some of them did elicit effector CD8 responses.

TABLE 4

| CMS5 and Meth A epitopes with highest NetMHC PWM scores | | | | | |
|---|---|---|---|---|---|
| Gene | Mut/WT Sequence | Mut/WT Score | Measured IC50 for $K^d$ Mut/WT | Immunogenicity | Tumor Protection |
| CMS5 Epitopes with the highest NetMHC scores | | | | | |
| Ssx2ip | CYAK(v/L)KEQL SEQ ID NO. 2/3 | 14.5/14.1 | 26/3.2 | + | − |
| Mapk1.1 | (q/K)YIHSANVL SEQ ID NO. 4/5 | 13.2/12.4 | 57/0.2 | − | − |
| Farsb | HY(v/L)HIIESKPL SEQ ID NO. 6/7 | 13/13.6 | 423/52 | + | − |
| Ncoa3 | (h/Q)YLQYKQEDL SEQ ID NO. 8/9 | 11.5/11.7 | 2162/54074 | − | − |
| Mapk1.2 | (q/K)YIHSANV SEQ ID NO. 10/11 | 11.4/10.7 | 2135/295 | − | − |
| Mapk1.3 | LYQILRGL(q/K)YI SEQ ID NO. 12/13 | 11.3/11 | 110/333 | − | − |
| Serinc1 | NYLLSLVAV(m/V)L SEQ ID NO. 14/15 | 11/10.2 | 2679/20861 | − | − |
| Meth A Epitopes with the highest NetMHC scores | | | | | |
| Usp12 | SY(l/R)VVFPL SEQ ID NO. 16/17 | 14.2/12.3 | 6835/1155 | − | − |
| Tfdp1 | QYSGS(w/R)VETPV SEQ ID NO. 18/19 | 14.2/15.3 | −*/603 | − | − |
| Ufsp2 | HYINM(i/S)LPI SEQ ID NO. 20/21 | 14.2/14.5 | 0.23/+++** | + | − |

TABLE 4-continued

CMS5 and Meth A epitopes with highest NetMHC PWM scores

| Gene | Mut/WT Sequence | Mut/WT Score | Measured IC50 for $K^d$ Mut/WT | Immunogenicity | Tumor Protection |
|---|---|---|---|---|---|
| Apc | AYCETCWE(l/W) SEQ ID NO. 22/23 | 14/8.1 | 23/60 | + | − |
| Hspg2 | SY(l/Q)LGSGEARL SEQ ID NO. 24/25 | 14/14.4 | 2623/79 | − | − |
| Ccdc85c | TYIRP(f/L)ETKV SEQ ID NO. 26/27 | 13.5/13.1 | 6155/118 | − | − |
| Pacs2 | HYLS(s/A)ILRL SEQ ID NO. 28/29 | 13.4/12.7 | 41/1269 | − | − |
| Alms1.1 | (l/S)YLDSKSDTTV SEQ ID NO. 30/31 | 13.3/15.2 | 79/16 | + | − |
| Alms1.2 | YYVPLLKRVP(l/S) SEQ ID NO. 32/33 | 13.3/7.3 | 421/1485 | − | − |
| Ckap5 | K(y/D)MSMLEERI SEQ ID NO. 34/35 | 13.2/1.7 | 17/7686 | − | − |
| Abr | GYFVSKAKT(s/R)V SEQ ID NO. 36/37 | 13.1/12.8 | 958/570 | + | − |

*—indicates IC50 >70,000 nM.
**+++indicates IC50 <0.1 nM.

In order to understand this unexpected result, and without being held to theory, we reasoned that the NetMHC score per se may not be a predictor of tumor-protective immunogenicity because it is conceivable that the un-mutated counterparts of these epitopes may themselves have good NetMHC scores: as a result, the T cell repertoire against the high scorers (and their mutated counterparts) may have been centrally deleted or peripherally tolerized. We therefore created a novel algorithm wherein the NetMHC scores of the un-mutated counterparts of the predicted mutated epitopes were taken into consideration by subtracting them from the corresponding NetMHC scores of the mutated epitopes. We refer to this new property of an epitope as its Differential Agretopic Index (DAI). The putative epitopes were now ranked on basis of the DAI (Table 5). A review of this DAI-ranked list for both tumors shows some curious aspects: (a) all the neoepitopes in this list show a mutation resulting in an amino acid change at one of the two anchor residues. (b) All of these changes are from Tyrosine to Aspartic Acid on position 2 or Leucine to Proline or Arginine on the Carboxy terminus. (c) The overwhelming majority of top-DAI-ranked neoepitopes have a NetMHC score below 8.72, the PWM peptide binding score threshold for weak binders for Kd (NetMHC3.0).

TABLE 5

CMS5 and MethA epitopes with highest DAI scores

| Gene | Mut/WT Sequence | Mut/WT Score | DAI | Measured IC50 for $K^d$ Mut/WT | Immunogenicity | Tumor Protection |
|---|---|---|---|---|---|---|
| CMS5 Epitopes | | | | | | |
| Dhx8.1 | P(y/D)LTQYAIIML SEQ ID NO. 38/39 | 9.3/−2.3 | 11.6 | 2192/1653 | + | − |
| Alkbh6.1 | D(y/D)VPMEQP SEQ ID NO. 40/41 | 4.3/−7.3 | 11.6 | 60858/− | − | − |
| Dhx8.2 | P(y/D)LTQYAI SEQ ID NO. 42/43 | 9.9/−1.6 | 11.5 | −*/− | − | − |
| Dhx8.3 | P(y/D)LTQYAII SEQ ID NO. 44/45 | 9.3/−2.2 | 11.5 | 244/1418 | − | − |
| Alkbh6.2 | D(y/D)VPMEQPR SEQ ID NO. 46/47 | 6.8/−4.7 | 11.5 | −/51229 | − | + |
| Dhx8.4 | P(y/D)LTQYAIIM SEQ ID NO. 48/49 | 6.6/−4.9 | 11.5 | 6571/6256 | − | − |
| Alkbh6.3 | D(y/D)VPMEQPRP SEQ ID NO. 50/51 | 4.8/−6.7 | 11.5 | −23570 | − | − |
| Alkbh6.4 | D(y/D)VPMEQPRPP SEQ ID NO. 52/53 | 4.7/−6.8 | 11.5 | 47053/2957 | − | − |

TABLE 5-continued

CMS5 and MethA epitopes with highest DAI scores

| Gene | Mut/WT Sequence | Mut/WT Score | DAI | Measured IC50 for $K^d$ Mut/WT | Immunogenicity | Tumor Protection |
|---|---|---|---|---|---|---|
| Rangap1 | SEDKIKAI(1/P) SEQ ID NO. 54/55 | 1.4/−5.4 | 6.8 | −/5108 | − | − |
| Stau1.1 | LKSEEKT(1/P) SEQ ID NO. 56/57 | 0.6/−6.2 | 6.8 | −/− | − | − |
| Stau1.2 | KPALKSEEKT(1/P) SEQ ID NO. 58/59 | 0.1/−6.7 | 6.8 | −/− | − | − |
| Stau1.3 | PALKSEEKT(1/P) SEQ ID NO. 60/61 | 1.3/−5.4 | 6.7 | 69546/− | − | − |
| Stau1.4 | ALKSEEKT(1/P) SEQ ID NO. 62/63 | 1.2/−5.5 | 6.7 | −/− | − | + |
| 9430016 H08Rik | SWSSRRSLLG(1/R) SEQ ID NO. 64/65 | 5.9/−0.6 | 6.5 | −/− | − | − |
| Slit3 | GFHGCIHEV(1/R) SEQ ID NO. 66/67 | 4.7/−1.8 | 6.5 | 51640/− | − | + |
| Atxn10.1 | QVFPGLME(1/R) SEQ ID NO. 68/69 | 3.4/−3.1 | 6.5 | −/7054 | + | + |
| Sipa1l3 | TTTPGGRPPY(1/R) SEQ ID NO. 70/71 | 2.7/−3.8 | 6.5 | −/− | − | − |
| Atxn10.2 | VFPGLME(1/R) SEQ ID NO. 72/73 | 2.5/−4 | 6.5 | −/1107 | − | + |
| Ccdc136 | ELQGLLEDE(1/R) SEQ ID NO. 74/75 | 2.4/−4.1 | 6.5 | −/4537 | − | + |
| Mast2 | KLQRQYRSPR(1/R) SEQ ID NO. 76/77 | 2.2/−4.3 | 6.5 | 10107/8511 | − | − |
| Meth A Epitopes | | | | | | |
| Tnpo3 | (sy/LD)MLQALCI SEQ ID NO. 78/79 | 8.2/−5.2 | 13.4 | 82/146 | + | + |
| Trim26.1 | A(y/D)ILAALTKL SEQ ID NO. 80/81 | 12.8/1.2 | 11.6 | 622/1.1 | − | − |
| Nus1 | P(y/D)LVLKFGPV SEQ ID NO. 82/83 | 10.5/−1.1 | 11.6 | 2359/1.9 | − | − |
| Tpst2.1 | L(y/D)EAGVTDEV SEQ ID NO. 84/85 | 10.3/−1.3 | 11.6 | 60/− | − | − |
| Fiz1 | H(y/D)LQGSNA SEQ ID NO. 86/87 | 10.3/−1.3 | 11.6 | 2473/− | − | − |
| Kdm4b | L(y/D)HTRPTAL SEQ ID NO. 88/89 | 10/−1.6 | 11.6 | 264/− | − | − |
| Dis3l2.1 | I(y/D)GVVARNRAL SEQ ID NO. 90/91 | 9.3/−2.3 | 11.6 | 143/− | + | − |
| Ube4a.1 | A(y/D)AKQFAAI SEQ ID NO. 92/93 | 9.3/−2.3 | 11.6 | 12/− | + | − |
| Ncdn | S(y/D)CEPALNQA SEQ ID NO. 94/95 | 8.9/−2.7 | 11.6 | 664/− | + | − |
| Gapdh | V(y/D)LTCRLEKPA SEQ ID NO. 96/97 | 8.9/−2.7 | 11.6 | 1150/− | − | − |
| Ckap5 | K(y/D)MSMLEER SEQ ID NO. 98/99 | 8.1/−3.5 | 11.6 | 58/− | − | − |
| Prrc2a | P(y/D)KRLKAEPA SEQ ID NO. 100/101 | 7.9/−3.7 | 11.6 | 1450/261 | − | − |
| Tmx3 | D(y/D)IIEFAHRV SEQ ID NO. 102/103 | 7.3/−4.3 | 11.6 | 7941/351 | − | − |

TABLE 5-continued

CMS5 and MethA epitopes with highest DAI scores

| Gene | Mut/WT Sequence | Mut/WT Score | DAI | Measured IC50 for K$^d$ Mut/WT | Immunogenicity | Tumor Protection |
|---|---|---|---|---|---|---|
| Nfkb1 | G(y/D)SVLHLAI SEQ ID NO. 104/105 | 6.9/−4.6 | 11.5 | 0.26/1615 | + | + |
| Dis3l2.2 | I(y/D)GVVARNRA SEQ ID NO. 106/107 | 6.9/−4.7 | 11.6 | 1342/262 | − | − |
| Ugdh | L(y/D)YERIHKKML SEQ ID NO. 108/109 | 6.4/−5.2 | 11.6 | 600/12 | − | − |
| Ml12 | S(y/D)RLPSSRKK SEQ ID NO. 110/111 | 5.9/−5.7 | 11.6 | 6673/17 | − | − |
| Galnt1 | L(y/D)VSKLNGP SEQ ID NO. 112/113 | 5.6/−6 | 11.6 | 27086/− | − | − |
| Tpst2.2 | L(y/D)EAGVTDE SEQ ID NO. 114/115 | 5.5/−6.1 | 11.6 | −/− | − | − |
| Cpsf2 | L(y/D)DVDAAF SEQ ID NO. 116/117 | 5.3/−6.3 | 11.6 | 1410/− | + | + |
| Zfp236.1 | E(y/D)LDLQTQ SEQ ID NO. 118/119 | 5.3/−6.3 | 11.6 | 1641/− | − | + |
| Trim26.2 | A(y/D)ILAALTKLQ SEQ ID NO. 120/121 | 4.9/−6.7 | 11.6 | 17599/− | − | − |
| Zfp236.2 | E(y/D)LDLQTQG SEQ ID NO. 122/123 | 4.9/−6.7 | 11.6 | 10028/− | − | − |
| Ube4a.2 | A(y/D)AKQFAA SEQ ID NO. 124/125 | 4.7/−6.9 | 11.6 | 28583/− | − | − |
| Dcaf6 | A(y/D)RLEGDRS SEQ ID NO. 126/127 | 3.7/−7.9 | 11.6 | −/− | − | − |

*—indicates IC50 >70,000 nM.

Figure 7:
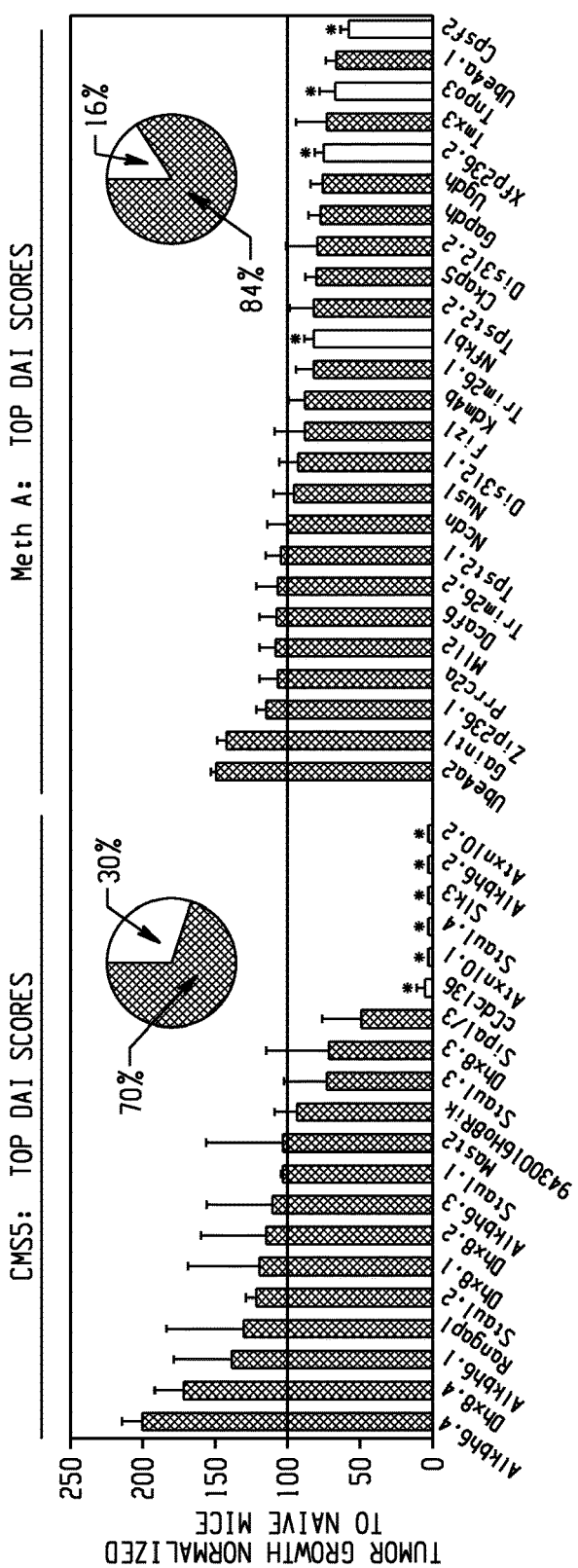
Figure 11:
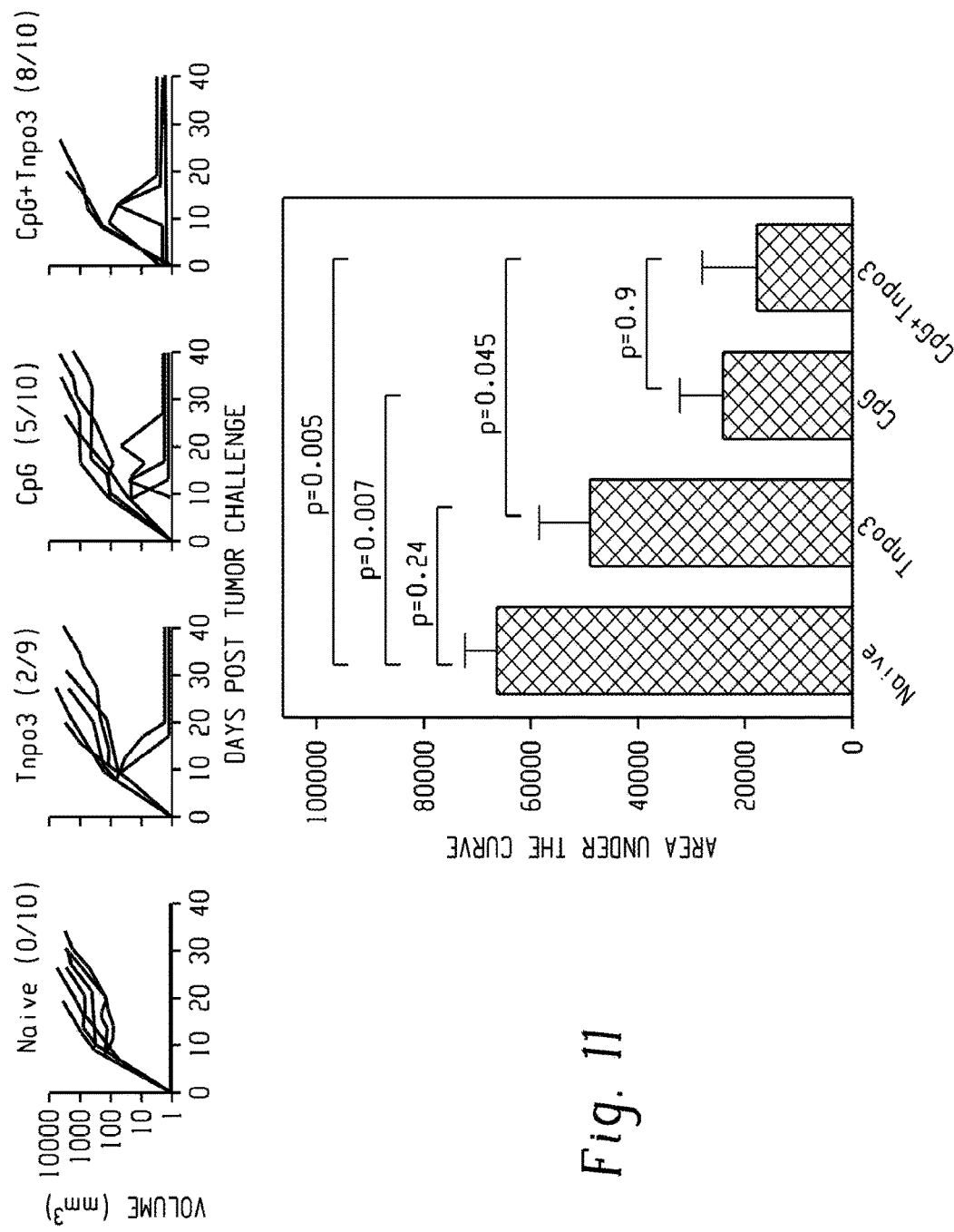
FIG. 11 shows the tumor-protective immunogenicity of the mutated Tnpo3 in mice that were unimmunized (naive) or injected with 50 μg CpG ODN1826 (CpG), 50 μg Tnpo3 peptide (Tnpo3), or both, and challenged with Meth A. (Top panel) Growth curves of tumors in individual mice are shown. The numbers in parentheses show the number of mice in which tumors regressed completely/total number of mice in that group. The bottom panel shows the AUC as a measure of tumor growth for each group.

The top DAI-ranking 20 epitopes of CMS5 and 25 epitopes of Meth A were tested in tumor rejection assays. The results (FIG. 7) show that 6/20 or 30% CMS5 epitopes and 4/25 or 16% Meth A epitopes showed statistically significant tumor protective immunogenicity (p-value 0.023). The statistical significance was evaluated using one-tailed Fisher's exact test by comparing the number of tumor protective epitopes among the set of epitopes selected by DAI and those selected by NetMHC score, 10/45 and 0/18, respectively. FIG. 8 shows some representative tumor rejection curves of two protective and one non-protective CMS5 epitope. (Corresponding curves on a Meth A epitope are shown in FIG. 11, along with a more detailed analysis of the activity of that epitope.) Although this algorithm yielded a far richer harvest of tumor-protective epitopes than the reliance on the highest NetMHC or MHC-binding scores (as in FIG. 6), most epitopes identified by our novel algorithm still fail to elicit tumor protection. Clearly, other properties of the putative epitopes, including perhaps the extent of direct presentation of the epitopes and the stability of the MHC-peptide complexes contribute to the tumor rejection activity. However, the measured K$^d$-binding of the epitopes as well as their ability to elicit T cell responses were observed to have no correlation with tumor-protective activity (P=0.45 for correlation of tumor rejection with K$^d$-binding and 0.27 for correlation of tumor rejection with immunogenicity). There are several examples of a lack of correlation between immunogenicity of an epitope and lack of its tumor-protective activity in clinical studies. Regardless of its imperfection, the DAI is a statistically significant and novel predictor of tumor-protective immunogenicity.

The tumor-protective immunogenicity of the epitope syMLQALCI (SEQ ID NO. 78) (wild type LDMLQALCI (SEQ ID NO. 79)), the mutated Transportin 3 (Tnpo3)-derived epitope, the highest ranking (by DAI) epitope of Meth A (Table 5), was investigated in more detail. Tnpo3 is a nuclear import receptor for serine/arginine rich protein encoded by a gene on mouse chromosome 6, and is not a driver protein for any tumor type reported thus far. The mutant Tnpo3 epitope was shown to elicit strictly tumor-specific CD8+ immune response, as seen by the ability of mutant Tnpo3-immunized mice to show strong tumor-specific reactivity to the mutant but not the wild type peptide ex vivo (FIG. 9). Conversely, CD8+ CD44+IFNγ+ cells isolated from mice immunized with Meth A tumor cells, recognize mutant Tnpo3-pulsed cells but not cells pulsed with an irrelevant K$^d$-biding peptide Prpf31 (FIG. 10). These observations confirm that the mutant Tnpo3 peptide is naturally presented by Meth A cells and also that immune response to it is elicited upon immunization by whole tumor cells. Interestingly, attempts to identify this mutant peptide by mass spectroscopic analysis of MHC I-eluted peptides from Meth A were unsuccessful, presumably because of the higher sensitivity of the T cell assays as compared to mass spectroscopy.

Figure 12:
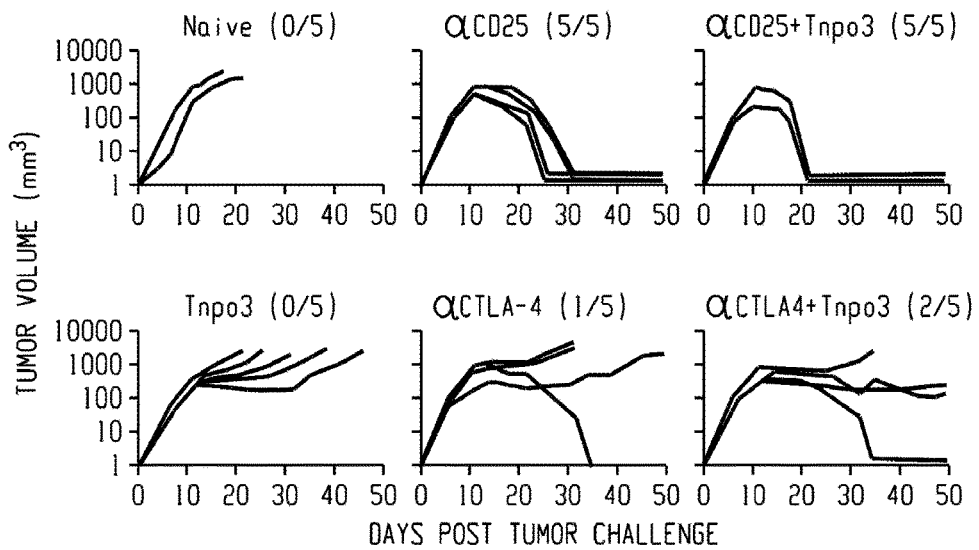
FIG. 12 shows the tumor-protective immunogenicity of the mutated Tnpo3 in mice that were unimmunized or immunized, as indicated, and were challenged. Anti-CD25 antibody (clone PC61, 250 μg, two days before tumor challenge) or anti-CTLA-4 antibody (clone 9D9, 100 μg, seven days before and every three days after tumor challenge) was given, as indicated. The bottom panel shows the AUC as a measure of tumor growth for each group.
Figure 12:
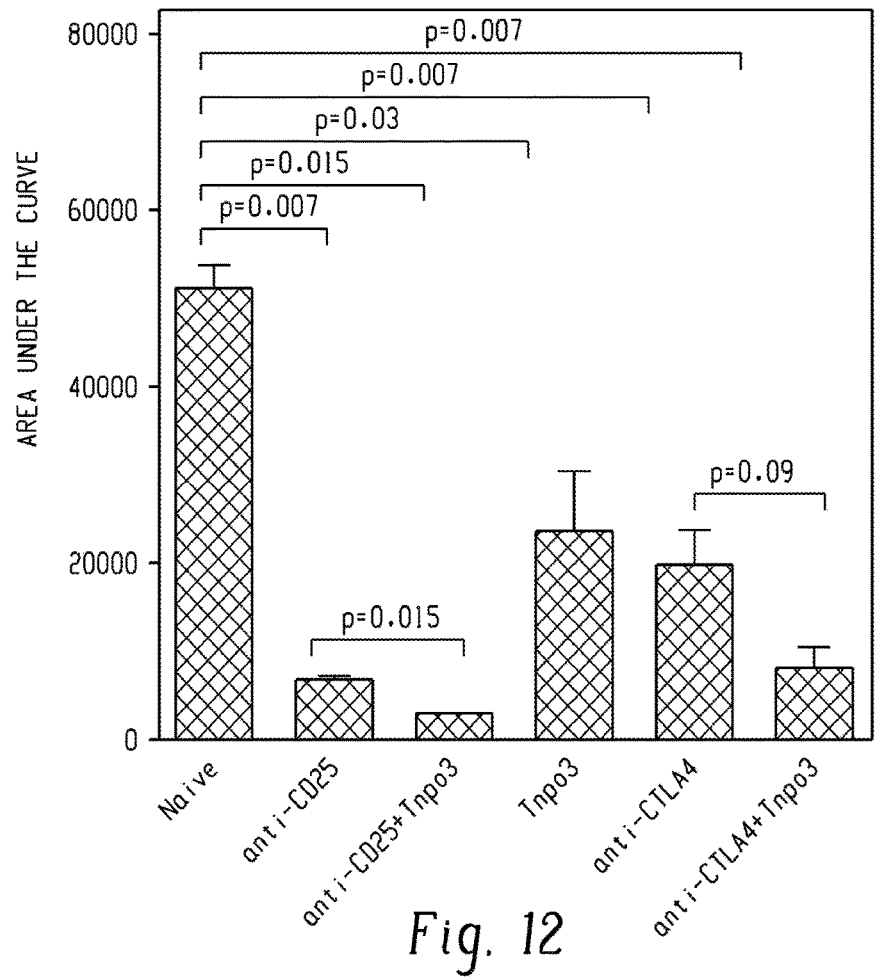

Example 5: Enhancement of Tumor-Protectivity of Neo-Epitopes by Immune Modulators The combination of immunization with mutant neoepitopes was tested using the Meth A neoepitope Tnpo3. This neoepitope is only modestly tumor protective in monotherapy, thus allowing more dynamic range for testing of an enhanced effect by combination therapy. As seen in FIG. 11, CpG alone elicited significant protection from tumor growth (P=0.007); mutated Tnpo3 alone elicited tumor rejection in 2/9 mice (as compared to 0/10 in naive mice), although the protection did not achieve statistical significance by the AUC in the experiment shown (P=0.24). However, a combination of the two elicited highly significant potent tumor protection (P=0.005 compared to un-immunized mice, and 0.045 compared to the mutant Tnpo3 immunized group). The protection from the combination as measured by AUC was not statistically significant over CpG alone (P=0.9), but the number of mice that rejected the tumor was much higher (8/10 in the combination compared to 5/10 in CpG alone). The combination of immunization with mutant Tnpo3 with antagonistic antibodies to CD25, which has been shown to target regulatory T-cells, also showed synergy; the anti-CD25 alone showed complete regression in all mice (P=0.007) and Tnpo3 alone too elicited significant protection (P=0.03). The combination showed more significant protection than either agent alone (FIG. 12). A similar result was obtained with the anti-CTLA4 antibody, which releases T cells from checkpoint blockade. Each agent alone elicited statistically significant protection and the combination was significantly more effective than Tnpo3 alone (FIG. 12). As measured by AUC, the combination was not statistically significantly more effective than the anti-CTLA4 antibody alone (P=0.09); however, the combination elicited complete tumor regression in 2/5 mice (as compared to 1/5 by the antibody alone), and prolonged tumor stabilization in 2/5 mice (as compared to 0/5 mice with the antibody alone).

Summary: The present disclosure shows a hidden treasure of truly tumor-specific antigenic epitopes; a significant proportion of the epitopes are actually tumor-protective in mouse models and their abundant existence in human tumors is corroborated from genomic data on human prostate cancers (Table 6) and melanomas (data not shown) as anticipated and modeled earlier. It is sobering to recognize that although T-cells clearly play a central role in immune response to cancer, T-cells appear to have been particularly poor probes for identification of immune-protective epitopes. Extensive analyses of tumor-specific antigens of Meth A and CMS5 sarcomas over the years managed to yield a total of five epitopes; in contrast, this single study has uncovered a minimum of nearly a dozen tumor-protective epitopes of these two tumors. It is instructive to ponder upon the reason for this discrepancy; the use of T-cells as probes inherently requires generation of T-cell lines or clones, which itself is a highly selective process. It would appear that the diversity of effector T-cells in vivo is not readily captured by the T-cell lines or clones generated, thus leading to a distorted, and sparse, view of the T-cell immunomes of tumors. The genomic analysis cuts through the bias in selection of T-cells and thus illuminates the entire field of neoepitopes.

TABLE 6

Summary of the high throughput transcriptome sequencing data and prediction of tumor-specific polymorphisms and epitopes for 14 human prostate cancer samples*

| | Somatic mutations reported in Ren et al. (11) | | | | | | | | | |
|---|---|---|---|---|---|---|---|---|---|---|
| | Synonymous/nonsynonymous in UCSC annotation | | Subset of nonsynonymous mutations within CCDS coding regions | | | | | NetMHC predicted epitopes | | |
| Tumor Sample | Synonymous | Non-synonymous | Total | Heterozygous | Missense | Nonsense | Total | A1101 | A2402 | A0201 |
| 1T | 7 | 10 | 10 | 10 | 9 | 1 | 9 | 4 | 0 | 5 |
| 2T | 4 | 3 | 2 | 2 | 2 | 0 | 4 | 4 | 0 | 0 |
| 3T | 7 | 4 | 3 | 3 | 3 | 0 | 10 | 5 | 1 | 4 |
| 4T | 5 | 3 | 3 | 3 | 3 | 0 | 2 | 2 | 0 | 0 |
| 5T | 4 | 7 | 7 | 7 | 7 | 0 | 18 | 12 | 2 | 4 |
| 6T | 3 | 5 | 5 | 5 | 4 | 1 | 3 | 1 | 0 | 2 |
| 7T | 2 | 3 | 2 | 2 | 2 | 0 | 2 | 1 | 1 | 0 |
| 8T | 20 | 44 | 40 | 40 | 38 | 2 | 82 | 42 | 7 | 33 |
| 9T | 13 | 22 | 18 | 18 | 16 | 2 | 30 | 13 | 0 | 17 |
| | | 36 | | | | | | | | |
| 10T | 20 | 32 | 29 | 29 | 28 | 1 | 36 | 20 | 3 | 13 |
| 11T | 6 | 13 | 9 | 9 | 9 | 0 | 17 | 8 | 2 | 7 |
| 12T | 3 | 11 | 10 | 10 | 10 | 0 | 28 | 13 | 5 | 10 |
| 13T | 2 | 5 | 5 | 5 | 5 | 0 | 9 | 2 | 3 | 4 |
| 14T | 19 | 32 | 29 | 29 | 24 | 5 | 53 | 25 | 8 | 20 |

*Calculated from published mutation data, and using the epitope prediction step of the Epi-Seq pipeline summarized in FIG. 1 to call the epitopes based on the mutation data.

Such neoepitopes for human cancers can now be identified in a cost-effective and time-sensitive manner, and may be used for immunotherapy. While tumor-protective epitopes can be identified, we cannot accurately predict whether a particular epitope will be tumor-protective. However, the demonstration that the DAI, the difference in the NetMHC scores of the mutated epitope and its unmutated counterpart is a good predictor, is the first key step in the right direction, and raises some stimulating new possibilities. Firstly, the demonstrated utility of the DAI score underscores the validity of its premise: that a tumor-protective immune response requires that the epitopes are more different from the normal, than that they be strong epitopes per se. Secondly, it stands to reason in hindsight that amino acid substitutions at the anchor residues make for the biggest differences, as seen in Table 5. However, the observation that some substitutions (such as Tyrosine to Aspartic Acid on position 2 or Leucine to Proline or Arginine on the Carboxy terminus) are so heavily preferred, is novel and suggests new avenues of structural enquiry. Finally, it is remarkable in our view that 10/10 neo-epitopes that elicit protective immunity are classified as weak binders by the criteria for such designation by NetMHC3.0. This observation may provide further clue to the basis of tumor-protective immunogenicity.

Further, the number of neoepitopes harbored by each tumor type is presently unknown but will be clear as more studies are pursued. The data on human prostate cancers (Table 6) suggest that these numbers may be small, and comparable to the numbers seen in spontaneous prostate cancers of mice (Table 1). On the other hand, the data on human melanomas (data not shown) suggests a much larger repertoire of epitopes. Several bases of such large differences in the numbers of neo-epitopes among human tumor can be imagined and tested.

Still further, the antigenic heterogeneity of cancers has been the subject of much discussion, but in lack of bona fide tumor-specific antigens in significant numbers, the debate has been largely theoretical. Uncovering of a large repertoire of true tumor-specific neo-epitopes now allows the questions regarding antigenic heterogeneity (and antigen escape) to be asked in an un-precedent and robust manner. A better resolution of this issue will allow increasing fine-tuning of the T cell epitopes to be used for immunotherapy of human cancers.

Inherently linked to the issue of antigenic heterogeneity is the role of immuno-editing of growing cancers. Following the classical studies on immune surveillance against tumors, it has been suggested that tumors go through elimination, equilibrium and escape phases of immuno-editing and have demonstrated evidence supporting the idea. The availability of a large repertoire of tumor-specific neo-epitopes of any given tumor allows immuno-editing to be addressed in far more granularity. Without being held to theory, it is believed that the quantity of non-synonymous mutations in a given tumor as a proportion of the total number of mutations is a good indicator of a tumor's place in the elimination-equilibrium-escape continuum is a testable prediction, which if true, can help guide the clinical management of cancer.

It has further been shown that immunization with neoepitopes can be combined effectively with a variety of immune-modulating agents including an innate stimulant (CpG), an anti-regulatory T cell agent (anti-CD25 antibody), and a checkpoint blockade antagonist (anti-CTLA4 antibody).

Altered peptide ligands have been used in cancer immunity as a means to enhance the immune response to self-epitopes that are overexpressed on tumors. The neoepitopes identified in our analyses are actually naturally generated altered peptide ligands for self-epitopes, and as such, can be imagined to elicit anti-self T-cell response. Any mouse or human studies should be alert to this possibility.

In addition to its influence on cancer immunity, the availability of a large number of tumor-specific neoepitopes dramatically enhances the scope of analysis of antigen presentation. Most of our knowledge of antigen presentation comes from the study of a handful of viral or model epitopes, and although these elegant and extensive studies have given us a wealth of information, the tens or hundreds of new epitopes provide additional opportunities, because of their variable properties. From among the epitopes identified herein, we have identified several, whose parent proteins appear to be well-expressed, which have excellent motifs for binding to MHC I, which elicit good CD8+ T cells upon immunization, and yet, which are not directly presented by the tumor cells. Analysis of their processing promises to identify novel steps, and the relative significance of existing pathways, in antigen presentation.

Lastly, it is intriguing that almost approximately 15% of the un-mutated epitopes are able to elicit effector CD8+ T cells upon immunization. To our knowledge, this study represents the first attempt, albeit un-intended, to test the immunogenicity of such a large number (n=119) of normal sequences. Apparently, CD8+ T cells against these epitopes did not undergo central deletion; alternatively, many of the normal sequences selected may represent cryptic epitopes that are never actually presented because of barriers to antigen processing. The two possibilities are amenable to experimental testing, and may shed light on relative significance of central and peripheral tolerance to self-antigens.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of identifying tumor epitopes in a cancer patient, comprising
   sequencing at least a portion of the cancer patient's RNA or DNA in both a healthy tissue and a cancer tissue, to produce a healthy tissue RNA or DNA sequence and a cancer tissue RNA or DNA sequence,
   comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set,
   analyzing the difference DNA marker set to produce a tumor-specific epitope set, wherein the tumor-specific epitope set comprises one or more tumor-specific epitopes, and wherein analyzing the difference DNA marker set to produce a tumor-specific epitope set is independent of whether one or more tumor-specific epitopes are related to cancer-causing pathways,
   calculating a numerical value called the Differential Agretopic Index for each tumor-specific epitope in the tumor-specific epitope set by subtracting a numerical score for a non-mutated amino acid sequence of the healthy tissue corresponding to the mutated amino acid sequence of the tumor-specific epitope from a numerical score for the tumor-specific epitope, wherein the numerical scores are calculated using an epitope predictive algorithm that predicts the binding of epitope peptides to MHC molecules,
   ranking the tumor-specific epitope set by the Differential Agretopic Index for each epitope in the set to identify a subset of 10 to 50 top-ranked tumor-specific epitopes,
   producing a pharmaceutical composition comprising a pharmaceutically acceptable carrier and one or more peptides comprising one or more tumor-specific epitopes selected from the subset of 10 to 50 top-ranked tumor-specific epitopes, or one or more polypeptides containing one or more tumor-specific epitopes selected from the subset 10 to 50 top-ranked tumor-specific epitopes, or one or more polynucleotides encoding one or more peptides comprising one or more tumor-specific epitopes selected from the subset of 10 to 50 top-ranked tumor specific epitopes, and wherein a non-mutated amino acid sequence of the healthy tissue corresponding to at least one of the one or more tumor-specific epitopes selected from the subset of 10 to 50 top-ranked tumor-specific epitopes has a negative numerical score, and
   optionally administering the pharmaceutical composition to the cancer patient.

2. The method of claim 1, wherein the sequencing is transcriptome sequencing.

3. The method of claim 1, wherein the sequencing is high-throughput sequencing.

4. The method of claim 1, wherein the pharmaceutical composition comprises one or more peptides comprising 1 to 100 tumor-specific epitopes from the tumor-specific epitope set, one or more polypeptides containing 1 to 100 tumor-specific epitopes from the tumor-specific epitope set, or one or more polynucleotides encoding 1 to 100 peptides comprising tumor-specific epitopes from the tumor-specific epitope set.

5. The method of claim 1, wherein the pharmaceutical composition comprises one or more peptides comprising 3 to 20 tumor-specific epitopes from the tumor-specific epitope set, one or more polypeptides containing 3 to 20 tumor-specific epitopes from the tumor-specific set, or one or more polynucleotides encoding 3 to 20 tumor-specific peptides comprising tumor-specific epitopes from the tumor-specific epitope set.

6. The method of claim 1, wherein the pharmaceutical composition further comprises an adjuvant.

7. The method of claim 6, comprising administering the pharmaceutical composition to the cancer patient.

8. The method of claim 1, wherein the pharmaceutical composition further comprises one or more immune-modulating agents.

9. The method of claim 7, wherein the immune-modulating agent is a TLR ligand or an antibody.

10. The method of claim 1, wherein the cancer patient is suffering from a solid cancer.

11. The method of claim 1, wherein the epitope predictive algorithm predicts the binding of epitope peptides of MHC molecules using artificial neural networks and weight matrices.

12. The method of claim 11, comprising administering the pharmaceutical composition to the cancer patient.

13. The method of claim 1, comprising administering the pharmaceutical composition to the cancer patient.

14. The method of claim 13, further comprising treating the cancer patient with radiation therapy, chemotherapy, surgery, or a combination thereof.

15. The method of claim 13, which further comprises mixing or pulsing the peptides, polypeptides, or polynucleotides with cells from the cancer patient, and wherein said administering further comprises administering the mixed or pulsed cells to the cancer patient.

16. The method of claim 1, which comprises, prior to the step of calculating the numerical value called the Differential Agretopic Index, a step of calculating (i) the numerical score for each tumor-specific epitope within the tumor-specific epitope set, and (ii) the numerical score for each non-mutated amino acid sequence of the healthy tissue corresponding to the mutated amino acid sequence of the tumor-specific epitope within the tumor-specific epitope set.

17. The method of claim 1, wherein the cancer patient is suffering from a liquid cancer.

* * * * *